US007276490B1

(12) United States Patent
Tanabe et al.

(10) Patent No.: US 7,276,490 B1
(45) Date of Patent: Oct. 2, 2007

(54) MEDICINAL COMPOSITIONS CONTAINING PROSTACYLIN SYNTHASE GENE

(75) Inventors: Tadashi Tanabe, 18-13, Higashitoyonaka-cho, 3-chome, Toyonaka-shi, Osaka (JP) 560-0003; Toshihisa Hatae, Saga (JP)

(73) Assignee: Tadashi Tanabe, Tokyo (JP)

( * ) Notice: Subject to any disclaimer, the term of this patent is extended or adjusted under 35 U.S.C. 154(b) by 431 days.

(21) Appl. No.: 10/296,555

(22) PCT Filed: Nov. 21, 2000

(86) PCT No.: PCT/JP00/08181

§ 371 (c)(1),
(2), (4) Date: Apr. 29, 2003

(87) PCT Pub. No.: WO01/89581

PCT Pub. Date: Nov. 29, 2001

(30) Foreign Application Priority Data

May 22, 2000  (JP)  .............................. 2000-150648

(51) Int. Cl.
*A61K 48/00* (2006.01)
(52) U.S. Cl. ..................... 514/44; 435/69.1; 435/320.1
(58) Field of Classification Search ..................... None
See application file for complete search history.

(56) References Cited

U.S. PATENT DOCUMENTS 5,814,509 A * 9/1998 Tanabe ....................... 435/233

FOREIGN PATENT DOCUMENTS

| WO | WO96/40128 | 12/1996 |
| WO | WO99/00491 | 1/1999 |

OTHER PUBLICATIONS

Kinoshita et al, Biochim Biophys Acta 1999; 1438: 120-30.*
Okahara et al, Arterioscler Thromb Vasc Biol 1998; 18: 1922-6.*
Crew et al, Carcinogen 2000;2:69-77.*
Tsujii et al, PNAS 1997;94:3336-40.*
Keith et al, FASEB J Mar. 15, 2000; 14(4):A474.*
Keith et al, Cancer Res 2002;62:734-40.*
Keith et al, Am J Respiratory Crit Care Med Mar. 1999; 159, No. 3, Supp. A206, (Best copy available).*
Bunn et al, The future of cyclooxygenase-2 inhibitors and other inhibitors of the eicosanoid signal pathway in the prevention and thearpy of lung cancer. Clin Lung Cancer 2002;3:271-277.*

Hatae, et al., The Molecular Biology Society of Japan, 22nd Annual Meeting, "A New Physiological Activity of Prostacyclin: G Protein Coupled Receptor (IP)-independent Pathway", pp. 268 (W41-5), (1999).
Bishop-Bailey, et al., "Endothelial Cell Apoptosis Induced by the Peroxisome Proliferator-activated Receptor (PPAR) Ligand 15-Deoxy-$\Delta^{12,14}$-prostaglandin $J_2$", vol. 274, No. 24, pp. 17042-17048 (1999).
Iwai, et al., "Human Prostacyclin Synthase Gene and Hypertension—The Suita Study", Circulation, vol. 100, pp. 2231-2236 (1999).
Numaguchi, et al., "Prostacyclin Synthase Gene Transfer Accelerates Reendothelialization and Inhibits Neointimal Formation in Rat Carotid Arteries After Balloon Injury", Arterioscler Thromb Vasc Biol., vol. 19, pp. 727-733 (1999).
Todaka, et al., "Gene Transfer of Human Protacyclin Synthase Prevents Neointimal Formation After Carotid Balloon Injury in Rats", Stoke, vol. 30, pp. 419-426 (1999).
He, et al., "PPARδ Is an APC-Regulated Target of Nonsteroidal Anti-Inflammatory Drugs", Cell, vol. 99, pp. 335-345 (1999).
Dusting, et al., "Nitric Oxide in Atherosclerosis: Vascular Protector or Villain?", Clin Exp Pharmacol Physiol Suppl, vol. 25, pp. S34-S41 (1998).
Kroll, et al., "Inhibition of Transforming Growth Factor-β1 and UV Light-Induced Apoptosis by Prostanoids in Prmary Cultures of Rat Hepatocytes", Toxicol Appl Pharmacol, vol. 152, pp. 240-250 (1998).

* cited by examiner

*Primary Examiner*—Q. Janice Li
(74) *Attorney, Agent, or Firm*—Townsend and Townsend and Crew LLP

(57) ABSTRACT

The present invention relates to: pharmaceutical compositions for inducing apoptosis in cells, the pharmaceutical compositions comprising a prostacyclin synthase gene as an active ingredient; pharmaceutical compositions for gene therapy of cancer, the pharmaceutical compositions comprising the above pharmaceutical compositions for inducing apoptosis as an active ingredient; and a screening method for an agent that induces apoptosis in a cell, the method comprising determining the activation of peroxisome proliferator-activated receptor (PPAR)-δ in the presence of a test substance. The pharmaceutical composition of the present invention for inducing apoptosis enables treatment of diseases on which induction of apoptosis has a therapeutic effect. In addition, the pharmaceutical composition of the present invention for gene therapy can lead cancer cells to cell death. Furthermore, the screening method of the present invention can be used conveniently to screen for agents capable of inducing apoptosis.

4 Claims, 20 Drawing Sheets

Caco-2

PGISwt           PGISC441A

HEK-293

PGISwt           PGISC441A

CV-1

PGISwt           PGISC441A

MEDICINAL COMPOSITIONS CONTAINING PROSTACYLIN SYNTHASE GENE

TECHNICAL FIELD

The present invention relates to pharmaceutical compositions for inducing apoptosis, which are useful for disease treatment where the induction of apoptosis produces therapeutic effects; pharmaceutical compositions for gene therapy, the pharmaceutical composition being useful for treating cancer; and screening methods for agents that induce apoptosis in cells.

BACKGROUND ART

Prostaglandin (PG) is a family of various eicosanoids derived from arachidonic acid (Vane, J. R. et al., Am. J. Cardiol. 75, 3A-10A (1995)). Arachidonic acid is converted into an endoperoxide intermediate, prostaglandin $H_2$ ($PGH_2$), by cycloxygenase. There are at least two types of isoforms of cyclooxygenase (COX-1 and COX-2). COX-1 is expressed constitutively in most tissues and cells; in some cases, the expression level is elevated during cell differentiation. In contrast, the expression of COX-2 is often up-regulated upon various types of stimulations (for example, mitogen, cytokine and endotoxin). Subsequently, the product $PGH_2$ produced by the action of COX is converted into various types of prostaglandins (e.g., $PGD_2$ and $PGF_2\alpha$ and prostacyclin ($PGI_2$)) as end products by specific synthases (Tanabe, T. et al., J. Lipid. Mediat. Cell Signal. 12, 243-255 (1995)). Prostaglandins produce a variety of effects in various aspects of regulation in homeostasis and pathogenesis. For example, $PGE_2$ regulates blood pressure, fertilization efficiency, and cell protection; prostacyclin not only contributes to the maintenance of cardiovascular system but also shows proliferation-inhibiting activity and cell-protecting activity. It has been reported that the overexpression of COX-2 in cells of epithelial cell line from gastrointestinal tract is associated with inhibition of apoptosis (Tsujii, M. et al., Cell 83, 493-501 (1995)) and $PGE_2$ is a major product in cells (Tsujii, M. et al., Cell 93, 705-716 (1998)). In contrast, the overexpression of COX-2 in an immortalized endothelial cell line results in retardation of cell proliferation and increases the frequency of cell death (Narko, K. et al., J. Biol. Chem. 272, 21455-21460 (1997)). Prostacyclin synthase (PGIS) is expressed endogenously in endothelial cells at high levels; prostacyclin is a major derivative of $PGH_2$ in cells (Kara, S. et al., J. Biol. Chem. 269, 19897-19903 (1994)).

It is known that the above-mentioned prostacyclin is an unstable lipid mediator whose half life is 5 to 10 minutes (Sinzinger, H. et al., Arch. Gynecol. Obstet., 243, 187-190 (1988)), and that prostacyclin plays important roles as a strong vasodilating substance and a strong endogenous inhibitor to platelet aggregation (Moncada, S. et al., N. Engl. J. Med. 17, 1142-1147 (1979)), which are presumed to be mediated by G protein-coupled receptor which increases the cAMP level (Smith, E. M. et al., J. Biol. Chem. 271, 33698-33704 (1996)). So far, prostacyclin is poorly characterized only by the presence of cell-protecting activity to various cells (for example, vascular endothelial cell, myocardial cell, gastric cell, hepatocyte, and renal cell) in addition to the well-known activity (Vane, J. R. et al., Am. J. Cardiol. 75, 3A-10A (1995)).

DISCLOSURE OF THE INVENTION

An objective of the present invention is to provide pharmaceutical compositions for inducing apoptosis, which are useful for disease treatment in which the induction of apoptosis produces therapeutic effects. Another objective of the present invention is to provide pharmaceutical compositions for gene therapy, the pharmaceutical compositions inducing apoptosis and thereby leading cancer cells to cell death. Yet another objective of the present invention is to provide screening methods for agents that induce apoptosis in cells, the method enabling conveniently screening for agents capable of inducing apoptosis.

Specifically, the present invention relates to:

(1) a pharmaceutical composition for inducing apoptosis in a cell, the pharmaceutical composition comprising a prostacyclin synthase gene as an active ingredient;

(2) a pharmaceutical composition for gene therapy of cancer, the pharmaceutical composition comprising the pharmaceutical composition according to (1) above as an active ingredient; and (3) a method of screening for an agent that induces apoptosis in a cell, the method comprising determining activation of peroxisome proliferator-activated receptor (PPAR)-δ in the presence of a test substance.

BEST MODE FOR CARRYING OUT THE INVENTION

Figure 1:
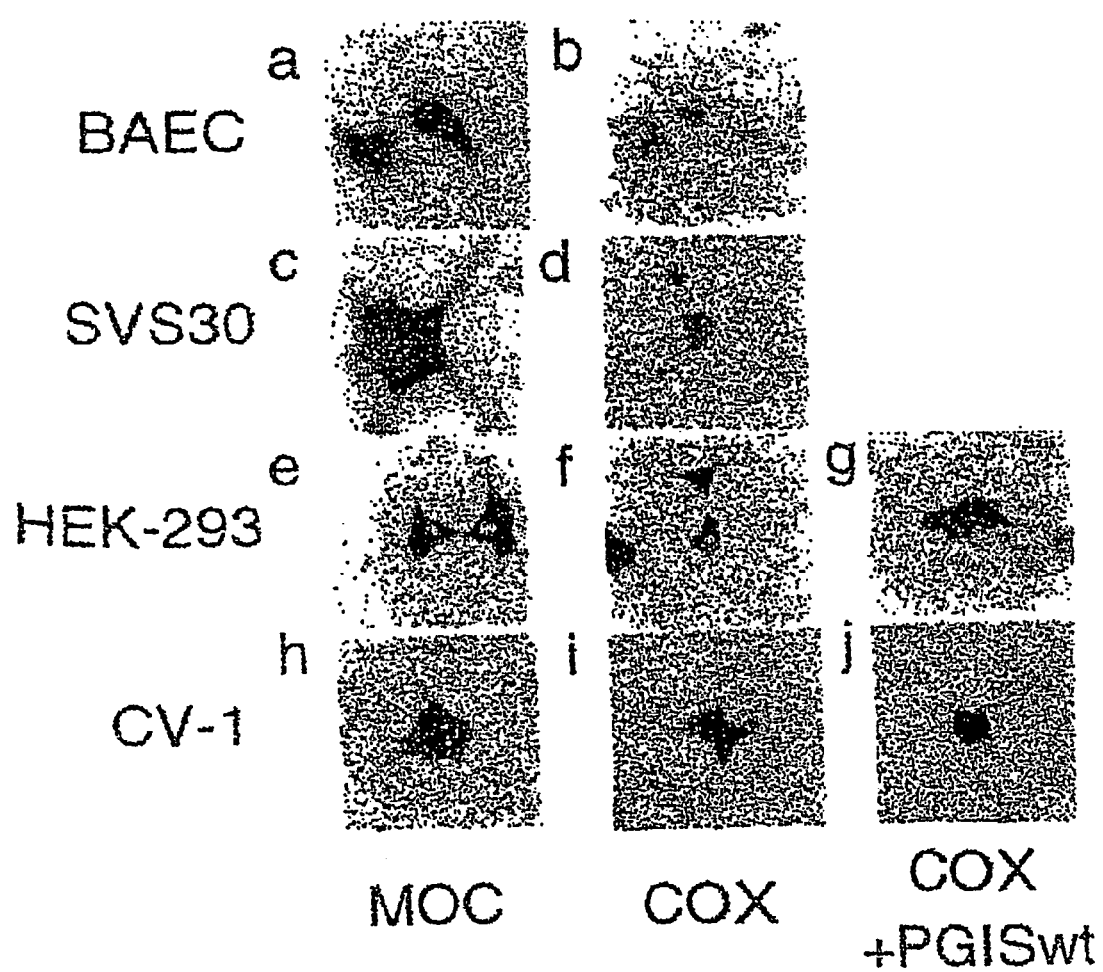
FIG. 1 shows photographic patterns indicating influences of COX-2 expression on BAEC cells, SVS30 cells, HEK-293 cells, and CV-1 cells. An expression vector for β-galactosidase was co-transfected into cells with a mock-transfection vector (a, c, e, h) or COX-2 expression vector (b, d, f, i), and then the cells were stained with X-Gal. An expression vector for wild-type PGIS (PGISwt) was co-transfected into HEK-293 cells (g) and CV-1 cells (j).

The present invention is based on the remarkable finding by the present inventors that intracellular prostacyclin produced by prostacyclin synthase in human kidney epithelial cell line 293 activates endogenous peroxisome proliferator-activated receptor-δ (PPAR-δ), which is a member of the nuclear hormone receptor superfamily, and the activation results in the enhancement of programmed cell death or apoptosis.

Specifically, the present inventors have found that intracellular prostacyclin produced by prostacyclin synthase in human kidney epithelial cell line 293 enhances programmed cell death or apoptosis by activating endogenous peroxisome proliferator-activated receptor (PPAR), which is a member of the nuclear hormone receptor superfamily. While the above-mentioned PPAR plays various roles in a variety of aspects in metabolism and homeostasis, there was extremely limited information about biological functions of PPAR-δ (Xu, H. E. et al., Mol. Cell. 3, 397-403 (1999)). In this study, the present inventors have found that the prostacyclin-mediated apoptosis is blocked by transfecting PPAR-δ antisense oligonucleotide according to the HVJ-liposome method. The present inventors have also found that the stimulation with extracellular prostacyclin or dbcAMP indeed results in not induction of apoptosis but suppression of apoptosis. These observations indicated that: (1) intracellular prostacyclin is a natural ligand for endogenous PPAR-δ; and (2) there is a second prostacyclin signaling pathway, which is mediated by PPAR-δ, and the pathway is associated with a reverse effect to the one exerted via cAMP pathway for cell fate control.

Based on the above-described finding, the present inventors have further found that, surprisingly, the introduction of the prostacyclin gene into cancer cells results in apoptosis of the cancer cells.

Peroxisome proliferator-activated receptor (PPAR) is a member of the nuclear hormone-receptor family and itself is a ligand-activated transcription factor (Nagy, L. et al., Cell 93, 229-240 (1998)). These receptors can be activated by lipid-reducing fibrates (for example, clofibrate), various types of fatty acids and some metabolites of arachidonic acid. The identified receptor includes three subtypes, namely PPAR-α, -δ (also known as PPAR-β or NUCI), and -γ (Braissant, O. et al., Endocrinology 137, 354-366 (1996)). PPAR is known to activate their target genes through the binding of a PPAR-RXR heterodimer to a DNA motif called PPAR-responsive element (PPRE) in the promoters of the target genes.

The biology of the PPAR-δ subgroup is most poorly understood among the PPARs; Iloprost and Carbacyclin have been reported to serve as ligands for recombinant PPAR-δ overexpressed in CV-1 (Forman. B. M. et al., Proc. Natl. Acad. Sci. USA 94, 4312-4317 (1997)). On the other hand, it had been unclear whether an unstable eicosanoid, prostacyclin, was a native ligand for endogenous PPAR-δ because of its instability. The present invention, however, demonstrated that for the first time.

1. Pharmaceutical Compositions for Inducing Apoptosis of Cells

The pharmaceutical compositions of the present invention for inducing apoptosis of cells comprise the prostacyclin synthase gene as an active ingredient. Accordingly, the introduction of a pharmaceutical composition of the present invention for gene therapy into target cells can result in intracellular production of prostacyclin, and thereby induces apoptosis in target cells; thus the composition show such an excellent effect. In addition, the half life of prostacyclin is as short as about 5 to 10 minutes, and when present outside cells, the prostacyclin does not induce apoptosis and instead shows cytoprotective activity; thus the composition shows an excellent effect of minimizing influences on cells surrounding the target cells.

The pharmaceutical composition of the present invention for inducing apoptosis includes those comprising the prostacyclin synthase gene as an active ingredient and to be used in combination with additional agents.

The additional agents include substances potentiating the ability of the above-mentioned prostacyclin synthase gene to induce apoptosis, substances allowing target cell-specific introduction, etc., and specifically include those containing the cycloxygenase-2 (COX-2) gene, those containing the cycloxygenase-1 (COX-1) gene, etc.

Apoptosis is a phenomenon characterized by: fragmentation of chromosomal DNA into nucleosomal fragments in cells; chromatin condensation; cell shrinkage; blebbing; loss of microvilli; cellar and nuclear fragmentation; and the formation of apoptotic bodies. The above-mentioned apoptosis can be assessed by testing for the above-mentioned characteristics of apoptosis, for example, detection of DNA ladders due to fragmentation by TUNEL method or electrophoresis; microscopic observation under a phase-contrast microscope; histological observation of fixed samples stained with hematoxylin, eosin or the like; observation of chromatin condensation to the perinuclear region under a fluorescence microscope after staining with aminobenzimide that is a DNA-binding fluorescent dye (for example, Hoechst 33342, Hoechst 33258, etc.), etc.

Further, caspase has been suggested to participate in the progress of apoptosis. Thus, caspase activity can be used as an index to assess the induction of apoptosis in cells.

(1) Prostacyclin Synthase Gene

There is no limitation on the origin of the prostacyclin synthase (hereinafter also referred to as PGIS) gene to be used in the present invention, including, for example, those from human, bovine, rat, etc.

The nucleotide sequence of the above-mentioned human PGIS gene (cDNA) and the amino acid sequence encoded by the nucleotide sequence have been disclosed, for example, in B.B.R.C., Vol. 200. No. 3, p 1728-1734 (1994) and international patent publication WO 95/30013. The bovine PGIS gene has also been reported in J. Biol. Chem., 269, 19897-19903 (1994); the rat PGIS gene has been described in Eur. J. Cell. Biol., 72, 268-277 (1997).

The PGIS genes to be used in the present invention can be cloned by carrying out RT-PCR, for example, using mRNA from vascular endothelial cells, and using appropriate DNA portions as PCR primers, based on the nucleotide sequence information provided in the above-mentioned references. Those skilled in the art can readily achieve the above-mentioned cloning, for example, according to any one of methods described in fundamental books, such as "Molecular Cloning; A Laboratory Manual 2nd Ed. Cold Spring Harbor Laboratory Press (1989)" (hereinafter called simply "Molecular Cloning").

In addition, the PGIS gene to be used in the present invention is not limited to those having the gene organizations described in the references indicated above, and includes those modified but retaining the activity.

Specifically, the prostacyclin synthase gene to be used in the present invention includes: (i) DNA hybridizing under stringent conditions to a cDNA of prostacyclin synthase as described in references indicated above, or (ii) DNA that encodes a protein comprising an amino acid sequence containing at least an alteration selected from the group consisting of substitution, deletion and addition of one or more amino acids in the amino acid sequence of prostacyclin synthase described in one of the above references, and is capable of inducing apoptosis when it is expressed in cells. The DNA described in (i) can be obtained by the standard hybridization technique; the DNA described in (ii) can readily be obtained, for example, by site-directed mutagenesis, PCR, etc. Specifically, such DNAs can be obtained by reference to the description in fundamental books including the above-mentioned "Molecular Cloning".

The "stringent conditions" include the hybridization conditions described in the above-mentioned "Molecular Cloning: A Laboratory Manual" (2nd Ed.)", and specifically includes the conditions in which hybridization is carried out under conditions comprising formamide concentration of 45% (V/V), salt concentration of 5×SSPE, and temperature of 42° C. and washing is carried out under conditions comprising salt concentration of 2×SSPE, temperature of about 42° C.

It can be confirmed that the polypeptide encoded by the DNA according to the above (i) or (ii) is a desired prostacyclin synthase according to an assay method for the activity of prostacyclin synthase; the presence or absence of the enzyme activity is determined by the assay and the activity is used as an index of the desired enzyme. Such assay methods for the activity include, for example, enzyme immunoassay using a 6-keto Prostaglandin F1α enzyme immunoassay kit (Cayman; catalogue number: #1515211) or a method of thin layer chromatography (TLC) for detecting the metabolite produced by prostacyclin synthase. It can also be confirmed that the polypeptide encoded by the DNA according to the above (i) or (ii) can induce apoptosis by introducing and expressing the DNA in cells and then subjecting the cells to one of various types of apoptosis assays, as described below in the Examples.

Further, the prostacyclin synthase gene to be used in the present invention may be: (iii) a DNA comprising a different nucleotide sequence from those of the prostacyclin synthase genes described in the above references due to the codon degeneracy.

(2) Cyclooxygenase-2 Gene

Furthermore, the present inventors found that the co-expression of the above-mentioned PGIS and cycloxygenase-2 (hereinafter abbreviated as COX-2) resulted in potentiation of the ability to induce apoptosis relative to the expression of PGIS alone.

There is no limitation on the origin of the COX-2 gene to be used in the present invention, including, for example, those from human, bovine, rat, etc.

The human COX-2 gene (cDNA) is described in Proc. Natl. Acad. Sci. USA, 89 (16), 7384-7388 (1992). The gene can be cloned based on the nucleotide sequence information described in the reference by the same procedure as used to clone the above-mentioned PGIS gene. Further, the COX-2 gene to be used in the present invention includes modified genes derived from the COX-2 gene described in the above reference when the modified ones exhibit the activity of COX-2 enzyme when expressed or exhibit the activity to potentiate the ability of the PGIS gene to induce apoptosis.

Specifically, the COX-2 gene to be used in the present invention includes: (I) DNA hybridizing under stringent conditions to a cDNA of cyclooxygenase-2 as described in references indicated above, or (II) DNA that encodes a protein comprising an amino acid sequence containing at least an alteration selected from the group consisting of substitution, deletion, and addition of one or more amino acids in the amino acid sequence of cycloxygenase-2 described in the above reference, and is capable of enhancing the ability of the PGIS gene to induce apoptosis, owing to its expression. The DNAs described in (I) and (II) can be obtained in the same way as described above for the PGIS gene.

The "stringent conditions" include the hybridization conditions described in the above-mentioned "Molecular Cloning: A Laboratory Manual (2nd Ed.)", and specifically includes the conditions in which hybridization is carried out under conditions comprising formamide concentration of 45% (V/V), salt concentration of 5×SSPE, and temperature of 42° C. and washing is carried out under conditions comprising salt concentration of 2×SSPE, temperature of 42° C.

It can be confirmed that the polypeptide encoded by the DNA according to the above (I) or (II) is a desired COX-2 based on the production of $PGH_2$ in the reaction using arachidonic acid as the substrate. The production of $PGH_2$ can be confirmed, for example, by a method using TLC (J. Biol. Chem., 274, 34141-34147 (1999), Proc. Natl. Acad. Sci. USA, 89, 7384-7388 (1992)). It can also be confirmed that the polypeptide encoded by the DNA according to the above (I) or (II) can induce desired apoptosis by introducing and expressing the DNA with PGIS gene in cells and then subjecting the cells to one of various types of apoptosis assays, as described below in the Examples.

(3) Method for Administrating Pharmaceutical Compositions for Inducing Apoptosis Administration methods of pharmaceutical compositions of the present invention for inducing apoptosis is roughly divided into two classes, (A) method using non-viral vector and (B) method using viral vector. For such administration methods, preparation methods, administration methods, and others are described in detail in experimental manuals (Basic Techniques for Gene Therapy, Experimental Medicine (Supplemental volume), Yodosha, 1996; Experiments of Gene Transfer and Expression Analysis, Experimental Medicine (Supplemental volume), Yodosha, 1997; Handbook for Development and Research of Gene Therapy (Ed. The Japanese society of Gene Therapy, NTS, 1999). Such methods are described specifically below.

A. Method Using Non-Viral Vector

The PGIS gene can be introduced into cells and tissues by one of the following techniques using a recombinant expression vector where the PGIS gene has been inserted in a conventional gene expression vector.

Methods for introducing genes into cells include calcium phosphate precipitation and direct DNA injection with glass micro-tubes.

Methods for introducing genes into tissues include gene transfer method using internal type liposome; gene transfer method using electrostatic type liposome; HVJ-liposome method; modified HVJ-liposome method (HVJ-AVE liposome method); receptor-mediated gene transfer method; method where DNA molecules are introduced into cells along with carrier (metal particles) by particle gun; method for directly introducing naked-DNA; transfer method using poly-cations, etc. A recombinant expression vector can be introduced into cells by one of the above methods.

Expression vectors that can be used in the present invention include, for example, pCAGGS (Gene 108, 193-200 (1991)), and pBK-CMV, pcDNA3.1 and pZeoSV (Invitrogen and Stratagene).

B. Method Using Viral Vector

The viral vector includes recombinant adenovirus, retrovirus, etc. More specifically, genes can be introduced into cells by inserting the PGIS gene of the present invention into a DNA virus or RNA virus, for example, attenuated retrovirus, adenovirus, adeno-associated virus, herpes virus, vaccinia virus, pox virus, poliovirus, Sindbis virus, Sendai virus, SV40, immunodeficiency virus (HIV), or the like, and then infecting the recombinant virus into cells.

The infectivity of adenovirus is known to be much higher than those of the other viral vectors among the above-listed viral vectors. Because of this, it is preferable to use the adenoviral vector system.

Methods of delivering a pharmaceutical composition of the present invention for inducing apoptosis into patients includes in vivo method where the pharmaceutical composition for inducing apoptosis is directly delivered into the body and ex vivo method where particular cells are collected from an human individual and the pharmaceutical composition for inducing apoptosis is introduced into the cells in vitro, which are returned into the body (Nikkei Science, April issue, 1994, pp 20-45; Gekkan Yakuji, 36(1), 23-48, 1994; Experimental Medicine (Special volume), 12(15), 1994; Handbook for Development and Research of Gene Therapy (Ed. The Japanese society of Gene Therapy; NTS), 1999). Preferred in the present invention is the in vivo method because apoptosis is induced in cells in which a pharmaceutical composition of the present invention has been introduced.

In the in vivo administration method, an administration route can be selected appropriately depending on the types of target cell, tissue, and organ where apoptosis is to be induced. The composition can be administered, for example, intravenously, intra-arterially, subcutaneously, intracutaneously, or intramuscularly, or directly to the lesions of local tissues.

There are various dosage forms for the composition depending on the type of administration route as described above (for example, solution, etc.). For example, when the composition is an injection containing a DNA as the active ingredient, the injection can be prepared according to the conventional method. For example, the composition can be prepared by dissolving the DNA in an appropriate solvent (buffer such as PBS, physiological saline, sterile water or the like), if required, sterilizing it with a filter, and filling a sterile vessel with the resulting solution. Such an injection can contain conventional carrier or the like as required. A liposome such as HVJ-liposome can be prepared as a liposome preparation such as suspension, cryogen, and cryogen concentrated by centrifugation.

To increase the level of the gene in lesions, a sustained release preparation (minipellet preparation, etc.) may be prepared and implanted near lesions, or alternatively a preparation can be administered gradually and continuously into lesions with an osmotic pump or the like.

The amount of DNA in the above-mentioned preparation can be adjusted appropriately depending on the type of disease to be treated, patient's age, weight, and others. For example, it is preferred that the amount of DNA as the active ingredient can be 0.0001 to 100 mg, preferably 0.001 to 10 mg. It is preferred that such a dose is given every several days or months.

A pharmaceutical composition of the present invention for inducing apoptosis can be evaluated pharmacologically, for example, by the procedure described below.

Animal Experiments

When a disease to be treated is cancer, a pharmaceutical composition can be evaluated pharmacologically by the following animal experiment. The composition are administered in adequate dose at appropriate frequency to nude mice as a cancer model in which tumor formation has been confirmed; an alteration in tumor diameters is observed at the same time. Control groups are: a group that is subjected to administration of DNA containing no prostacyclin synthase gene, and a group that is subjected to administration of DNA containing an inactive prostacyclin synthase gene where a site-specific mutation(s) has been introduced. Further, to assess the dose or frequency of administration, one can use several different groups where the dose or frequency of administration is varied appropriately. Once tumor formation is confirmed, then tumor size is measured in both group subjected to the administration of the pharmaceutical composition of the present invention for inducing apoptosis (treated group) and control group. When tumor involution is seen in the treated group, the involution serves as an index of therapeutic achievement of cancer therapy at the level of animal experiment. In addition, tissues can be assessed by the above-described method for assessing characteristics of apoptosis. When many apoptotic cells are seen in the treated group, the presence of apoptotic cells serves as an index of apoptosis-inducing activity of the pharmaceutical composition of the present invention for inducing apoptosis at the level of animal experiment.

Clinical Test in Human

The viral vector should be tested for the cytotoxicity, infectivity to other individuals and integration into the chromosome of viral vector, when one intends to use the prostacyclin synthase gene inserted into a viral vector or the like. These methods and therapeutic method can be conducted, for example, by reference to the descriptions in the above-mentioned "Handbook for Development and Research of Gene Therapy (Ed. The Japanese society of Gene Therapy; NTS, 1999)" and others. When target cells are cancer cells, clinical effects on individuals can be evaluated, for example, by the following methods. Namely, photographic images, CT scan images, MRI images or the like of tumors are recorded periodically, thereby measuring diameters of tumor. Tumor volumes are estimated based on the orthogonal major and minor axes to determine tumor growth rates. The therapeutic effects are evaluated based on an assessment index depending tumor type. Additionally, the presence of apoptosis is assessed by morphological observations on the tissues. Further, analysis techniques of molecule biology can be utilized; the presence of a DNA as the active ingredient in target cells can be confirmed by the detection method using PCR; apoptosis can be detected by TUNEL staining.

2. Pharmaceutical Compositions of the Present Invention for Gene Therapy of Cancer When introduced into cells, the prostacyclin synthase gene produces prostacyclin in the cells and thus shows an excellent effect of inducing apoptosis of the cells. Accordingly, when introduced into cancer cells, the prostacyclin synthase gene induces apoptosis in the cancer cells and thus can be used to treat cancers. In addition, the half life of prostacyclin is as short as about 5 to 10 minutes, and when present outside cells, the prostacyclin does not induce apoptosis and instead shows cytoprotective activity. Thus, when the prostacyclin synthase gene is introduced specifically into cancer cells, harmful influences on cells other than cancer cells can be reduced; such an excellent effect can be produced by the prostacyclin synthase gene. The present invention thus provides a pharmaceutical composition for gene therapy of cancer, the pharmaceutical composition containing the above-mentioned prostacyclin synthase gene as an active ingredient. In other words, the present invention also includes a pharmaceutical composition for gene therapy of cancer, the pharmaceutical composition comprising as an active ingredient the pharmaceutical composition for inducing apoptosis described in the above Section 1.

The pharmaceutical composition of the present invention for gene therapy includes those comprising the above-mentioned prostacyclin synthase gene as an active ingredient and to be used in combination with additional agents.

The "additional agents" include substances potentiating the ability of the above-mentioned prostacyclin synthase gene to induce apoptosis, substances allowing specific delivery of the above-mentioned prostacyclin synthase gene into cancer cells, etc., and specifically include those containing the cycloxygenase-2 (COX-2) gene, those containing the cancer cell-specific surface antigen, those containing the cycloxygenase-1 (COX-1) gene, or the like.

The prostacyclin synthase gene and the COX-2 gene that can be used in the present invention include the same as those indicated in the above Section 1.

The pharmaceutical composition of the present invention for gene therapy of cancer can be used to treat every cancer type, and in particular, can be used to treat COX-2-highly-expressing cancers more effectively. Such cancer includes solid cancer.

In general, approximately 70% of cancer cells are COX-2-highly-expressing type, namely, cells that express COX-2 at enhanced levels. Caco2 cell used in the Examples described below is also a cell line derived from COX-2-highly-expressing cancer cells. Such COX-2-highly-expressing cancer cells may be treated by gene therapy with the PGIS gene alone, or alternatively the induction of apoptosis can be further enhanced by using PGIS in combination with the COX-2 gene.

On the other hand, when cancer cells express endogenous COX-2 at low or undetectable levels, it is preferable to conduct gene therapy using the PGIS gene and COX-2 gene in combination in order to maximize the effect of cancer therapy with enhanced induction of apoptosis.

It is preferable to selectively deliver a pharmaceutical composition of the present invention for gene therapy into cancer cells to reduce or avoid influences on cells surrounding the cancer cells.

Method for achieving selective gene transfer into and gene expression in cancer cells are described in detail, for example, in "Handbook for Development and Research of Gene Therapy (Ed. The Japanese society of Gene Therapy; NTS, 1999) and others. Specific examples of such methods are described below in [1] to [5].

[1] Retroviral Vector-Mediated Delivery

Transfer of the retroviral vector is restricted to dividing cells. Based on this property, the pharmaceutical composition of the present invention for gene therapy can be introduced selectively into cancer cells proliferating rapidly. In particular, this method is useful to administer the vector into ventricular cavities in brain tumor patients. Specifically, this can be achieved by using, as the pharmaceutical composition for gene therapy of cancer, a recombinant retroviral vector which has been prepared by inserting the PGIS gene into the above-mentioned retroviral vector so as to express PGIS. Further, when the "additional agent" mentioned above is, for example, the COX-2 gene, it can be achieved by co-expressing both COX-2 gene and PGIS. For example, it can be achieved by using a pharmaceutical composition containing both recombinant retroviral vector prepared by introducing the COX-2 gene into the above-mentioned retroviral vector and the recombinant retroviral vector containing the above-mentioned PGIS.

[2] Gene Transfer Using Mutant Adenovirus Strain

Recently, McCormick et al. of ONYX Co. has developed a mutant adenovirus strain that kills specifically cancer cells (Nature Med., 3 (6), 639-645 (1997)). This mutant adenovirus strain cannot infect to cells in which p53 functions, but can replicate in p53-deficient cells. 50% or more of cancer cells have no p53 activity.

Using this method to deliver a pharmaceutical composition of the present invention for gene therapy, the PGIS gene can be introduced selectively into p53-deficient cancer cells. Specifically, this can be achieved by using, as the pharmaceutical composition for gene therapy of cancer, a recombinant mutant adenoviral vector prepared by inserting the PGIS gene into the above-mentioned mutant adenoviral vector so as to express PGIS. Further, when the "additional agent" mentioned above is, for example, the COX-2 gene, it can be achieved by co-expressing both COX-2 gene and PGIS. For example, it can be achieved by using a pharmaceutical composition comprising both the above-mentioned recombinant mutant adenoviral vector containing the COX-2 gene and the recombinant mutant adenoviral vector containing PGIS.

Furthermore, genes can be targeted into pRB-deficient cancer cells using an adenoviral vector. Like p53 activity, pRB activity is lost in many cell types (Nature Med., 3(10), 1145-1149, (1997)). This method can also be used in the present invention.

[3] Gene Transfer Using Cancer Cell-Specific Surface Antigens as Targets

Selective transfer of genes into cancer cells can be achieved using, as targets, cancer antigens expressed specifically on the surface of cancer cell and antigens (transferrin receptor, EGF receptor, etc.) that are also expressed in normal cells but at much higher levels particularly in cancer cells. Specific examples of such methods include the following <1> to <3>.

<1> Gene Transfer Using Immunoliposome Coupled with a Monoclonal Antibody Against to an Antigen A previous report describes transfer of specific genes into glioma cells using immunoliposome where plasmid (DNA) is encapsulated in liposome coupled with an antibody against the cells (Cancer Res., 50, 7826-7829 (1990)).

A pharmaceutical composition of the present invention for gene therapy can be introduced specifically into cancer cells by using immunoliposome obtained by encapsulating a pharmaceutical composition of the present invention for gene therapy in liposome coupled with a monoclonal antibody against a cancer cell-specific surface antigen.

<2> Transferrin Receptor-Mediated Gene Transfer

As described above, transferrin receptor is expressed abundantly on the surface of cancer cells, and thus cancer cell-specific targeting can be achieved by using the receptor. Such methods include, for example, method using DNA complex comprising transferrin and plasmid linked to each other via biotin-avidin-biotin (Ann. NY Acad. Sci., 716, 336-337 (1994)) and method using transferrin-liposome-DNA complex, etc.

Specifically, for example, DNA complex comprising the PGIS gene expression vector and transferrin linked to each other via biotin-avidin-biotin or the like can be used as an active ingredient in a pharmaceutical composition of the present invention for gene therapy.

<3> EGF Receptor-Mediated Gene Transfer

Since EGF receptor is also expressed abundantly on the surface of cancer cells, it can be used to target genes into cancer cells. An exemplary method is immunogene method using the complex of a monoclonal antibody against EGF receptor and plasmid cross-linked via polylysine (Cancer Gene Ther., 3, 113-120 (1996)). Another established method uses the complex of EGF and DNA linked to each other (Cancer Gene Ther., 3, 4-10 (1996)).

In the present invention, for example, the complex of monoclonal antibody against EGF receptor and the PGIS gene expression vector cross-linked via polylysine or complex of EGF and the gene expression vector linked to each other can be used as an active ingredient for a pharmaceutical composition of the present invention for gene therapy.

In addition, for example, a report describes a method for targeting to hepatocytes using the complex between DNA and polylysine linked to asialylated sugar chain of galactose, which was designed based on the fact that the expression of asialoglycoprotein receptor is restricted to hepatocyte (J. Biol. Chem., 266, 14338-14342 (1991)). This method can be used effectively to treat hepatic cancers.

Specifically, for example, the complex between an expression vector for the PGIS gene and polylysine linked to asialylated sugar chain of galactose, or the like, can be used as an active ingredient of a pharmaceutical composition for gene therapy of the present invention.

[4] Targeting Using Cancer Cell-Specific Promotor

The targeting to cancer cells can be achieved by using a vector system (promotor/enhancer system) that directs specific expression in cancer cells.

Specifically, a vector where the above-mentioned prostacyclin synthase gene is ligated to and controlled by one of various promotors as listed in Table 1 on page 505 in "Handbook for Development and Research of Gene Therapy (Ed. The Japanese society of Gene Therapy; NTS, 1999), i.e., cancer cell-specific promotor such as AFP promotor (hepatic cancer), CEA promotor (stomach cancer, pancreatic cancer), DF3 promotor (breast cancer), osteocalcin promotor (osteosarcoma), or the like, can be used as an active ingredient of a pharmaceutical composition for gene therapy of the present invention.

[5] Method for Directly Injecting Genes into Local Sites

The simplest method for delivering a gene into specific cells is an ex vivo method which comprises collecting target cells (cancer cells) from a patient, introducing genes into the purified cells, and returning the cells to the patient.

On the other hand, an in vivo method currently used in clinical tests is the in situ gene transfer method for directly introducing vectors into local sites. Some examples have be reported, including percutaneous direct injection of the HLA-B7 gene into melanoma in skin using cationic liposome as the carrier (Proc. Natl. Acad. Sci. USA. 90, 11307-11811 (1993)) and injection of a p53 gene-containing viral vector into lung cancer percutaneously or via a bronchoscope (Nature Med., 2, 985-991 (1996)).

In the present invention, one can also use an in situ gene transfer method for directly introducing an expression vector containing the above-mentioned prostacyclin synthase gene into local sites. It is preferable to ensure selectivity of transfer to cancer cells by using the in situ gene transfer method in combination with the above-mentioned methods of [1] to [4] in order to achieve high efficiency specific transfer to target tissues and cells.

Prostacyclin is known to exert the cell-protecting effect via a G protein-coupled receptor on the cell membrane (Am. J. Cardiol., 75, 3A-10A (1995)). Accordingly, it can be predicted that prostacyclin released from cells in which the PGIS gene has been introduced shows cell-protecting activity toward surrounding normal tissues. Hence, a pharmaceutical composition of the present invention comprising the PGIS gene as an active ingredient can be a therapeutic agent for cancer showing fewer side effects as compared to other agents.

A pharmaceutical composition of the present invention for gene therapy of cancer can be evaluated pharmacologically, for example, by the same procedure as used to evaluate the above-mentioned pharmaceutical composition for inducing apoptosis.

3. Screening Method for Agents that Induce Apoptosis in Cells

The present inventors have revealed an entirely new mechanism in which intracellular prostacyclin produced via the introduction of the PGIS gene activates peroxisome proliferator-activated receptor (PPAR)-δ and thereby induces apoptosis. Based on this new finding, the present invention provides a screening method for agents that induces apoptosis, the method comprising using activation (including binding) of PPAR-δ as an index.

The screening method of the present invention for agents that induce apoptosis in cells comprises determining activation of peroxisome proliferator-activated receptor (PPAR)-δ in the presence of a test substance. Substances capable of inducing apoptosis based on the above-mentioned mechanism can be selected conveniently by using the screening method.

The screening method of the present invention includes any types of methods as long as they allow contact between PPAR-δ and a test substance and further assay and evaluation for PPAR-δ activation.

Specifically, the screening method of the present invention for agents that induce apoptosis in cells include: (embodiment 1) a method that comprises contacting a test substance with transformed cells harboring a plasmid in which a PPAR-responsive element (PPRE) and a reporter gene has been ligated, and that comprises using an increase in the expression level of the reporter gene as an index of ability of the test substance to induce apoptosis; and (embodiment 2) a method that comprises contacting a test substance with peroxisome proliferator-activated receptor (PPAR)-δ in vitro. The methods of embodiments 1 and 2 are described below.

Method of Embodiment 1

First, a plasmid is prepared in which a sequence containing the PPAR-responsive element PPRE is ligated with a reporter gene. Such a sequence containing PPRE includes the oligonucleotide containing three copies of PPRE as described in the Example. The reporter gene includes genes such as luciferase, CAT (chloramphenicol acetyl transferase), ALP (alkaline phosphatase), or GH (growth hormone). Various promoter vectors, which contain any of the above-mentioned reporter genes and a promotor such as SV40, β-globin, thymidine kinase, or the like are commercially available; any of those are usable. Specifically, such a vector includes pGL3-promoter vector (Promega).

Then, the above-mentioned plasmid is introduced into cells to prepare transformed cells. There is no limitation on the type of cell to be used as the host, so long as it expresses PPAR-δ endogenously and allows detection of the reporter gene activity. Specifically, such cells include HEK-293 cell (ATCC CRL-1573) used in the Example. Further, methods for delivering the plasmid into cells include calcium phosphate method, method using LT-1 (Panvera), and method using LipofectAMINE (Gibco-BRL).

Transformed cells prepared as described above may be cells transiently expressing the reporter gene in the above-mentioned plasmid, or cells stably containing the reporter gene (stable transformants). In particular, stable transformants are preferred cells because gene delivery is not always required at every screening and thus screening can be carried out more simply in a shorter time.

A candidate for the agent induces apoptosis can be selected by adding a test substance to transformed cells thus prepared, and measuring and assessing whether the test substance raises the expression level of the reporter gene. A test substance that increases the expression level of the reporter gene is a candidate for the agent that induces apoptosis. Thus, an agent that induces apoptosis in cells can be selected by further subjecting such selected candidate test substances to apoptosis assay using, as an index, caspase activity as described in the Example.

Method of Embodiment 2

A test substance is contacted with purified PPAR-δ in vitro to measure and assess whether the two bind to each other. The purified PPAR-δ can be obtained by cloning and expressing the PPAR-δ gene (Endocrinology, 137, No. 1, 354-366 (1996); Proc. Natl. Acad. Sci. U.S.A., Vol. 91, 7355-7359 (1994)) according to the conventional methods.

The binding between the purified PPAR-δ and a test substance can be determined, for example, by the fluorescence polarization assay using Full-Range BEACON 2000 from PanVera, or the like. Alternatively, such binding can be detected by examining whether a test substance competitively inhibits the binding between labeled prostacyclin or a derivative thereof (Iloprost, etc.) and PPAR-δ purified or immunoprecipitated.

An agent that induces apoptosis in cells can be selected by subjecting candidate test substances, which have been selected by such a screening method, to the same apoptosis assay as described above.

Herein below, the present invention will be specifically described using Examples, however, it is not to be construed as being limited thereto.

[EXAMPLE 1] EXPERIMENTAL PROCEDURES (1) Preparation of Antibodies and Double-Staining Using an Anti-PGIS Antibody and Hoechst 33258

The synthesis peptides P1 (PGEPPLDLGSIPWLGY-ALDC; SEQ ID NO: 1) corresponding to a segment of amino acids at position 27 to 45 in human PGIS in and P4 (LMQPEHDVPVRYRIRP; SEQ ID NO: 2) corresponding to a segment of amino acids at position 485 to 500 that is linked to keyhole lympet hemocyanin were prepared by Peptide Institute Inc. Japanese albino rabbits were immunized with 1 mg of peptide combined with Freund's complete adjuvant. Both antisera against P1 and P4 were suitable for immunoblotting experiments. In this study, the antiserum against P1 was used in immunoblotting, and the P4 antiserum was used in immuno-fluorescence staining.

Cultured monolayer cells of human fetal kidney-derived HEK-293 cell line (ATCC CRL-1573) were harvested and plated in Dulbecco's modified Eagle's medium containing 10% bovine fetal serum (FBS), 100 U/ml penicillin, and 100 mg/ml streptomycin ($3\times10^5$ cells/60-mm dish). 24 hours after incubation, the cells were transfected with 3 µg of any one of PGISwt (described below), PGISC441A (described below), or control vector pCMV7 (generous gift from Texas University; Andersson, S. et al., J. Biol. Chem., 264, 8222-8229 (1989): this can be replaced with pcDNA3 (Invitrogen; catalogue number: #A-150228)) and 0.3 mg of pvA (plasmid encoding adenovirus-associated RNA1) using LipofectAMINE (Gibco-BRL). 5 hours after transfection, the cells were rinsed twice with phosphate-buffered physiological saline (PBS), and the fresh medium was added thereto. After gene transfer, the cells were cultured for 48 to 60 hours in total. Then, the cells were rinsed with PBS, and fixed with 3.7% formaldehyde for 10 minutes. The cells fixed were washed three times with PBS, and then incubated with the anti-PGIS antibody P4 for 2 hours. After being washed three times with PBS containing 2% FBS, the cells were incubated with anti-rabbit Ig-Texas Red at 37° C. for 1 hour and stained with 1 mM Hoechst 33258 at room temperature for 15 minutes.

(2) Oligonucleotides and HVJ-Liposome Method

The following oligonucleotides were prepared by ESPEC oligo service Co. Ltd.:

dS, which corresponds to human PPAR-δ cDNA sense sequence: 5'-CTCGGTGACTTATCCTGTG-3' (SEQ ID NO: 3); dAS, which corresponds to human PPAR-δ cDNA antisense sequence: 5'-TCCTCTTTCTCCTCCTCTT-3' (SEQ ID NO: 4); aS, which corresponds to human PPAR-α cDNA sense sequence: 5'-CTCGGTGACTTATCCTGTG-3' (SEQ ID NO: 5); and aAS, which corresponds to human PPAR-α cDNA antisense sequence: 5'-CACAGGATAAGT-CACCGAG-3' (SEQ ID NO: 6). These oligonucleotides were transfected into cells by HVJ-liposome method. Each oligonucleotide (22 µg) was combined with a nuclear protein and high mobility group (HMG)-1. HVJ-liposome was prepared by combining dry lipid (phosphatidyl serine/phosphatidyl choline/cholesterol (1:4.8:2 w/w/w)) with ultraviolet light-inactivated HVJ virus (viruses). After incubation and centrifugation with a sucrose-density gradient, the top layer was collected for transfection. 48 hours after transfection, cells in which the expression of endogenous PPAR-δ had been suppressed were used in PPREx3-luciferase assay and apoptosis assay.

(3) PPREx3-Luciferase Assay

The sense oligonucleotide CGCGTAAAAACTGGGC-CAAAGGTCTCAAAAACTGGGCCAAAG-GTCTAAAAACTGGGCCAAAGGT CTC (SEQ ID NO: 7) and antisense oligonucleotide TCGAGAGACCTTTGGC-CCAGTTTTTAGACCTTTGGCCCAGTTTT-TAGACCTTTGGCCCAGTTTT A (which contains three copies of PPRE; SEQ ID NO: 8) were synthesized and annealed together; the resulting double-stranded DNA was subcloned into PGL3-promoter vector (Promega) at the MluI-XhoI site. PPREx3-luciferase reporter vector and β-galactosidase expression vector were co-transfected into HEK-293 cells using LipofectAMINE. The activity of β-galactosidase was normalized with absorbance at 405 nm.

(4) Apoptosis Assay

Cells were transfected with 1.0 µg of β-galactosidase expression vector using LipofectAMINE. After a fixed time, the cells were stained with X-Gal to evaluate the cells for apoptotic morphology. Apoptosis was monitored with ApoAlert caspase assay kit using Ac-DEVD-AFC substrate (Clontech). The activity was determined by using lysate pretreated with. Ac-DEVD-CHO as a control according to the supplier's instructions. The caspase activity is defined as a ratio between the caspase activity of a sample and that of lysate prepared from HEK-293 cells mock-transfected with a control plasmid.

Results

The present inventors found that the overexpression of COX-2 in bovine aortic endothelial cells (BAEC) or murine vascular smooth muscle SVS30 cells resulted in significant morphological changes including membrane vesicle formation and cell body shrinkage (typical features of apoptosis) (Yang, X. et al., Cell 89, 1067-1076 (1997)) (FIGS. 1b and 1d). On the other hand, transfection of the COX-2 expression vector to human fetal kidney epithelial cell line 293 (HEK-293) or monkey kidney CV-1 cells resulted in no alteration (FIGS. 1f and 1i). While BAEC and SVS30 express endogenous PGIS, neither HEK-293 nor CV-1 express PGIS. However, the relationship between apoptosis and PGIS still remained unclear at this stage.

Figure 2:
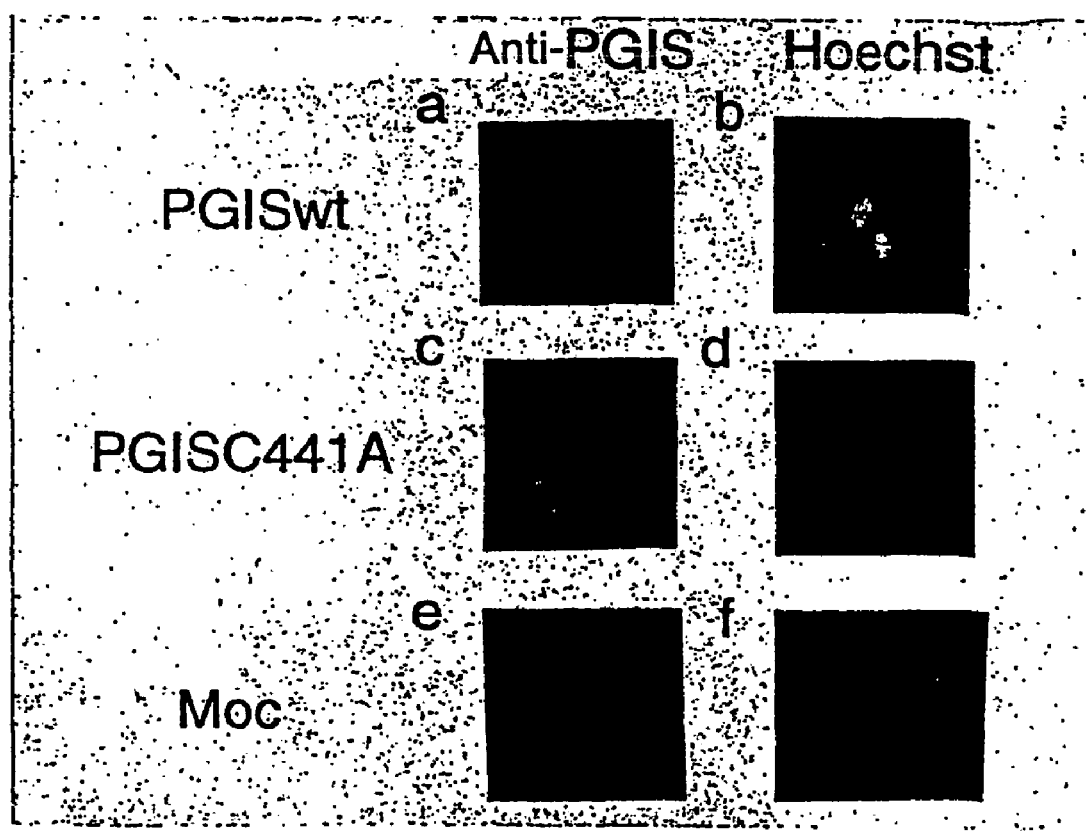
FIG. 2 shows photographic patterns indicating influences of the expression of wild-type PGIS (PGISwt) or inactive PGIS (PGISC441A) on human fetal kidney epithelial cell line HEK-293. The wild-type PGIS (PGISwt) enhanced apoptosis in HEK-293. The cells were transfected with a PGISwt expression plasmid (a, b), expression plasmid for inactive PGIS (PGISC441A) (c, d), or negative control mock plasmid (e, f). The cells were fixed with 3.7% formaldehyde, and then double-stained with anti-PGIS polyclonal antibody P4 (a, c, e) and fluorescent dye bis-benzimide (Hoechst 33258)(b, d, f). PGISwt (a) and PGISC441A (c) expressed in the cells were detected immunologically using a Texas-red-conjugated secondary antibody.
Figure 3:
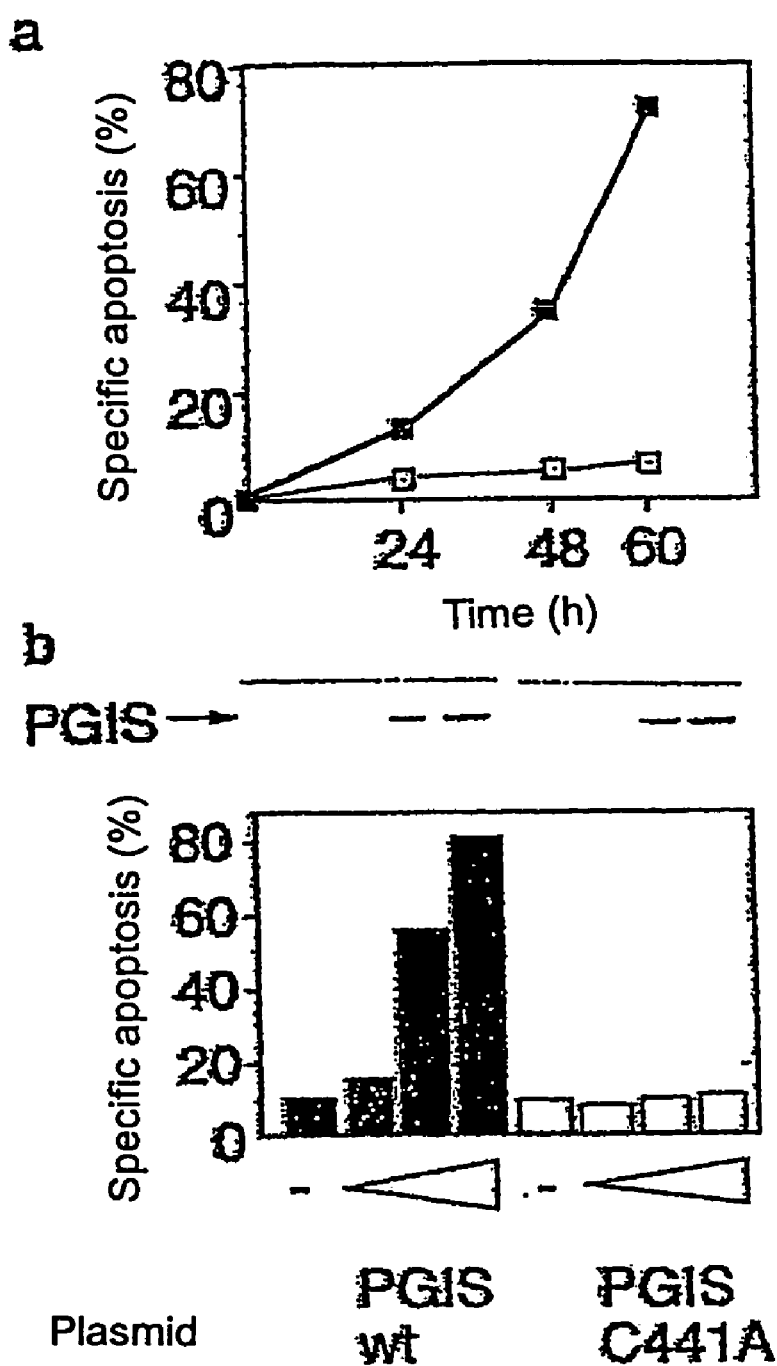
FIG. 3 shows diagrams indicating: (a) the time course of % ratio of apoptosis in anti-PGIS positive cells and Hoechst 33258 positive cells, and (b) an influence of increased amount of PGISwt or PGISC441A expression plasmid on apoptosis. In the upper part of panel (b), the expressed PGISs (PGISwt and PGISC441A) were detected by immunoblotting analysis using an anti-PGIS antibody P1. Percentage of apoptotic cells was increase being in correlation with the amount of PGISwt protein expressed in the cells (the bottom part of panel (b)).

Thus, to test whether apoptosis depends on the expression of PGIS, an expression plasmid for PGIS and a COX-2 expression vector were co-transfected into HEK-293 cells or CV-1 cells. As seen in FIGS. 1g and 1j, the morphology of both cell lines was drastically changed. To test the possibility that prostacyclin produced by PGIS is associated with induction of apoptosis, HEK-293 was transfected with an expression vector for enzymatically active wild-type human PGIS (PGISwt) or inactive mutant PGISC441A (a mutant PGIS enzyme in which a mutation has been introduced at Cys residue in the active site of PGIS by site-directed mutagenesis) (Hatae, T. et al., FEES Lett. 389, 268-272 (1996)). Immuno-fluorescence staining using an anti-PGIS polyclonal antibody was carried out to confirm the expression of PGIS in the cells. Concurrently, fluorochrome bis-benzimide (Hoechst 33258) dye staining was carried out to detect the presence of a typical apoptosis-associated morphological change, chromatin condensation. The expression of PGISwt significantly reduced the cell viability and normality as compared to control cells. As shown in FIGS. 2a and 2b, it was found that PGIS-positive cells expressing PGISwt protein were specifically stained with Hoechst 33258. The genomic DNA extracted from these cells showed a ladder pattern (data not shown). As FIG. 2c shows, the expression level of mutant PGIS was found to be similar to that of wild-type enzyme by immuno-fluorescence staining, but PGIS-positive cells expressing PGISC441A protein was not stainable with Hoechst 33258 (FIGS. 2c and 2d). As shown in FIG. 3a, the increase in the number of apoptotic Hoechst 33258-positive cells was time-dependent. Furthermore, as compared to the number of PGIS-expressing cells, the number of Hoechst-33258 positive cells was reduced by treating the cells with 100 μM U46619 (PGIS inhibitor) (Zou, M. et al., Biol. Chem. 378, 707-713 (1997))(32%) or 100 μM aspirin (COX inhibitor) (48%) (data not shown). With increasing the amount of the PGISwt expression vector used to transfect the cells, the level of PGISwt protein expressed in cells, which was detected by immunoblotting, and the number of apoptotic cells was both increased being in correlation with each other (FIG. 3b). On the other hand, when PGISC441A expression vector was transfected into cells under the same conditions, the number of apoptotic cells was not increased, but the degree of increase in the expression level of PGISC441A protein was comparable to that of PGISwt. These results suggest that the expression of active PGIS is requisite for the chromatin condensation in HEK-293 cells.

Figure 4:
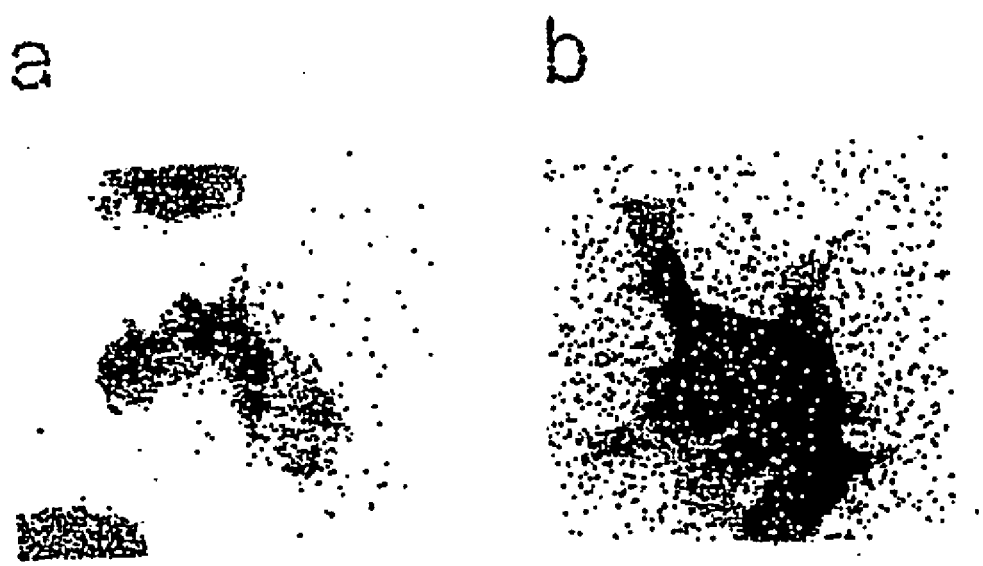
FIG. 4 illustrates photographic patterns showing results of co-transfection of the expression construct for β-galactosidase with another construct for PGISwt (a) or PGISC441A (b) into cells.
Figure 5:
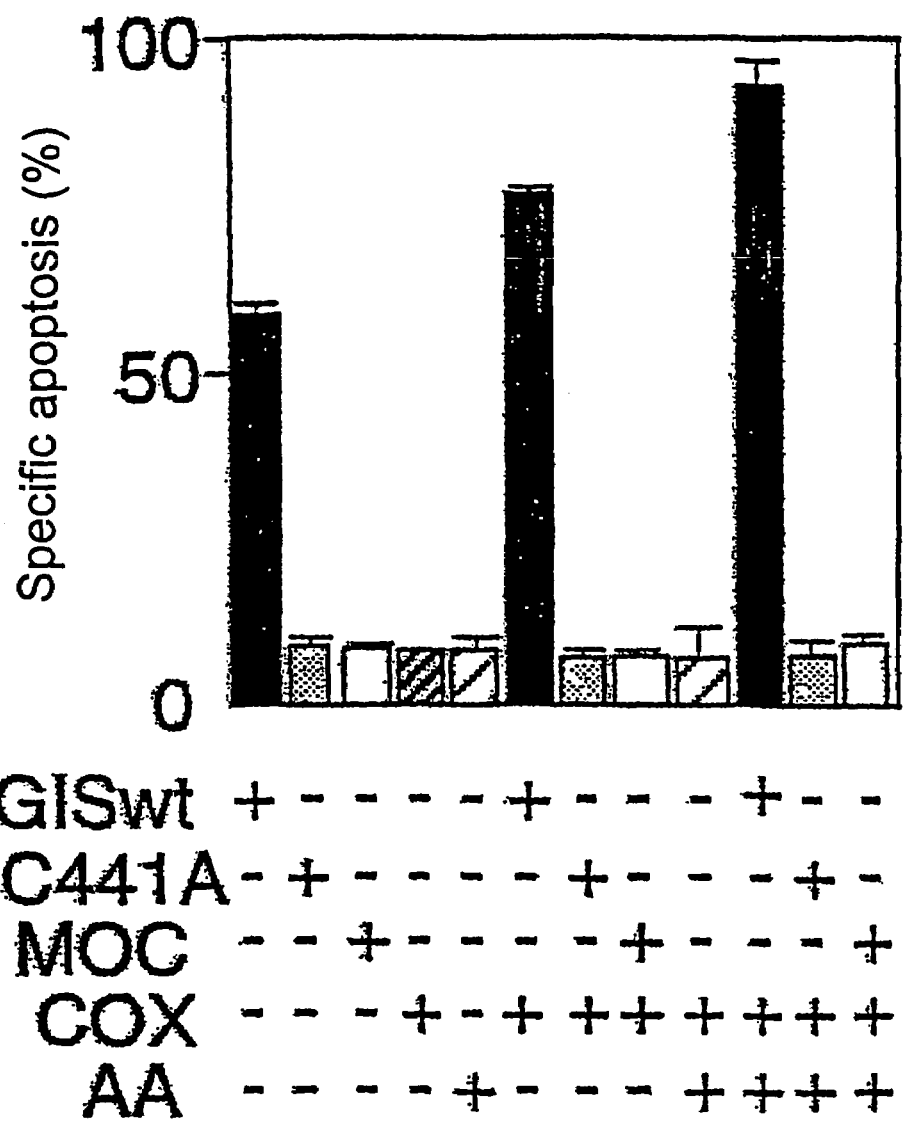
FIG. 5 shows a diagram indicating percentage of apoptotic cells in total cells to which the indicated expression constructs had been transfected. The cells were transfected with expression vectors for β-galactosidase, COX-2, and for PGISwt or PGISC441A or a mock expression vector in combination as shown in FIG. 5 in the presence or absence of arachidonic acid, followed by determination of the percentage ratio of cells stained blue with apoptotic morphology (for example, membrane vesicle formation and cell body shrinkage) to total cells stained blue. All results were obtained from three sets of experiments (n=3) and are presented as mean±S.D.
Figure 6:
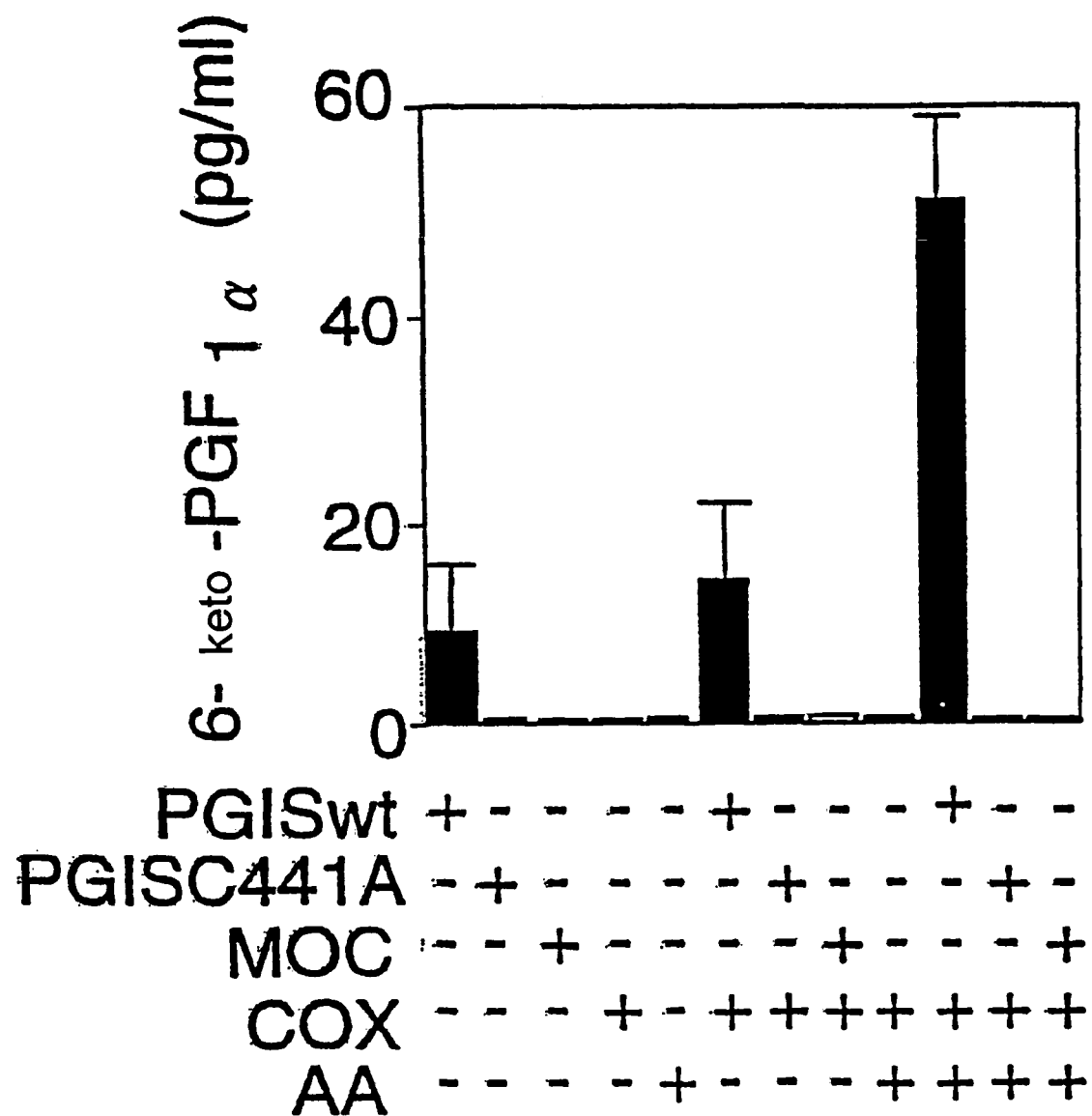
FIG. 6 shows a diagram indicating levels of 6-keto-PGF$_1$α determined for the respective cells to which the indicated expression constructs had been transfected. All results were obtained from three sets of experiments (n=3) and are presented as mean±S.D.

To strictly ascertain the relationship between the expression of PGIS and apoptosis, HEK-293 cells were co-transfected with two types of expression constructs for human PGISwt and β-galactosidase. Because normal HEK-293 cells have flat morphology, it is easy to assess the cells for apoptotic changes characterized by membrane vesicle formation and cell body shrinkage. After incubation for a predetermined time following transfection, cells were stained with X-gal for β-galactosidase activity to identify cells containing the transgenes and then assessed for the apoptotic morphology. After 60 hours, drastic morphological changes associated with apoptosis were observed specifically in the cells stained blue at a significant level (FIG. 4a). In contrast, when the cells were transfected with the PGISC441A expression vector, no morphological change was observed (FIG. 4b). These results suggest that the expression of enzymatically active PGIS is requisite for apoptosis in the cells. In HEK-293 cells, apoptosis was induced only by the expression of PGISwt without the presence of co-expression of COX-2 (FIGS. 4a and 5). The co-expression of COX-2 with PGISwt increased the number of apoptotic cells (16%). Furthermore, addition of arachidonic acid to the medium resulted in the induction of apoptosis in almost all the cells expressing both PGISwt and COX-2. The level of 6-keto-PGF$_1$α released into culture medium was correlated with the frequency of apoptosis (FIG. 6). The co-expression of COX-1 instead of COX-2 gave a similar result (data not shown). When the PGISC441A expression vector was used in transfection, the production of 6-keto-PGF$_1$α was not detected and the number of cells showing morphological changes did not increase (FIGS. 5, 6, and 4b). Neither co-expression of PGISC441A and COX-2 nor further addition of arachidonic acid gave influence on the production 6-keto-PGF$_1$α and morphological changes (FIGS. 5 and 6). These findings clearly indicate that prostacyclin produced by active PGIS participates in the process of apoptosis.

Figure 7:
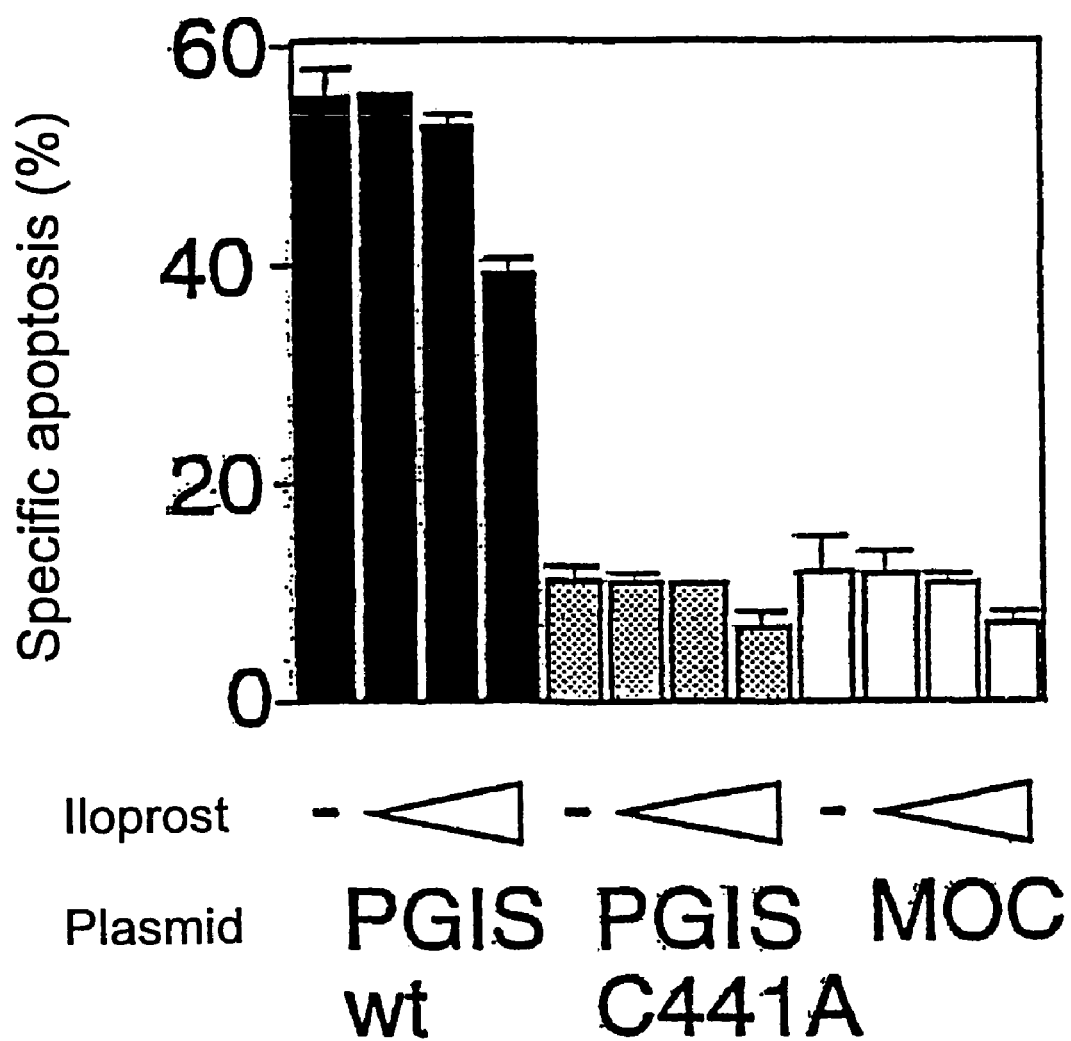
FIG. 7 illustrates a diagram showing the percentage ratio of specific apoptotic cells in serum-free medium containing Iloprost at the concentrations indicated (0, 1, 10, or 100 μM). The cells were transfected with expression plasmids for PGISwt, PGISC441A, or a mock control expression plasmid and β-galactosidase expression plasmid. After 17 hours, the medium was changed with serum-free medium containing Iloprost at various concentrations (0, 1, 10, or 100 μM). All results were obtained from three sets of experiments (n=3) and are presented as mean±S.D.
Figure 8:
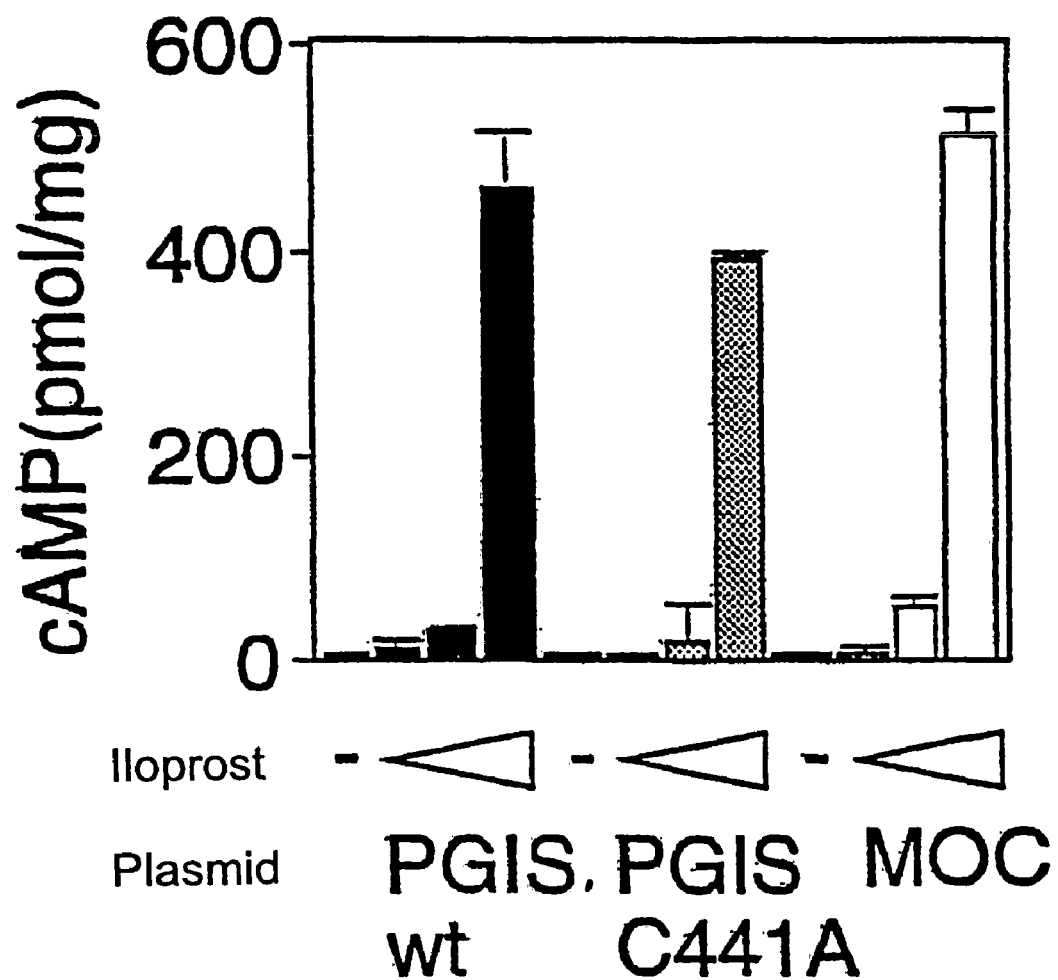
FIG. 8 illustrates a diagram showing the intracellular level of cAMP accumulated in cells in serum-free medium containing Iloprost at the concentrations indicated (0, 1, 10, or 100 μM). The cells were transfected with expression plasmids for PGISwt, PGISC441A, or a mock control expression plasmid and β-galactosidase expression plasmid. After 17 hours, the medium was changed with serum-free medium containing Iloprost at various concentrations (0, 1, 10, or 100 μm). All results were obtained from three sets of experiments (n=3) and are presented as mean±S.D.
Figure 9:
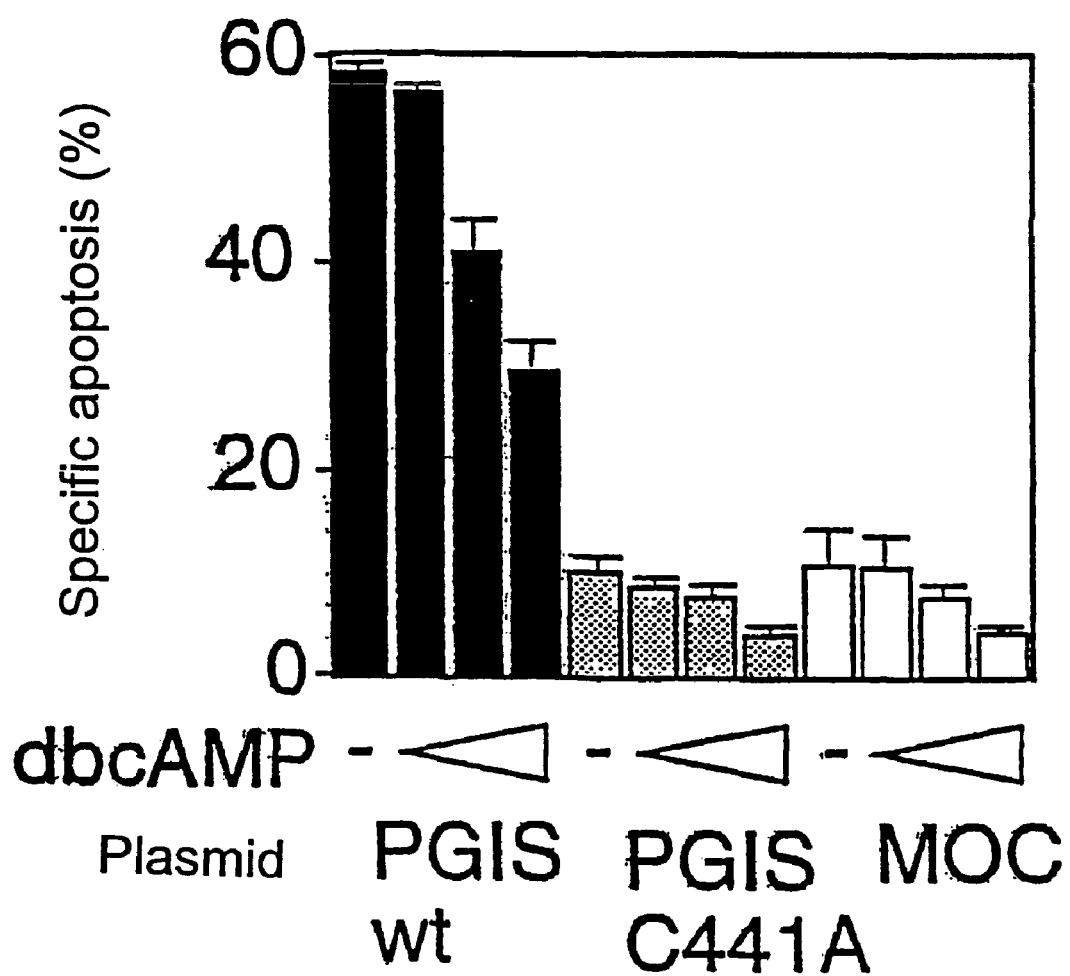
FIG. 9 illustrates a diagram showing the percentage ratio of specific apoptotic cells in serum-free medium containing dbcAMP at the concentrations indicated (0, 1, 10, or 100 μM). The cells were transfected with expression plasmids for PGISwt, PGISC441A, or a mock control expression plasmid and β-galactosidase expression plasmid. After 17 hours, the medium was changed with serum-free medium containing dbcAMP at various concentrations (0, 1, 10, or 100 μM). All results were obtained from three sets of experiments (n=3) and are presented as mean±S.D.
Figure 10:
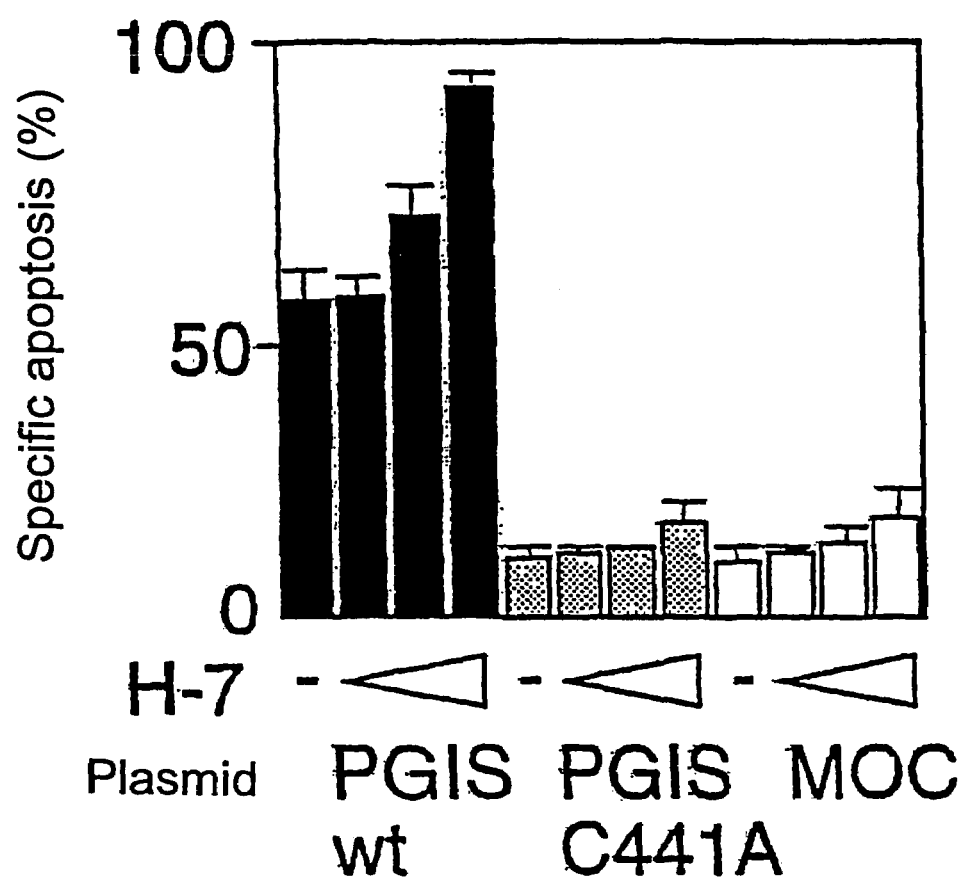
FIG. 10 illustrates a diagram showing the percentage ratio of specific apoptotic cells in serum-free medium containing dbcAMP at the concentrations indicated (0, 1, 10, or 100 μM). The cells were transfected with expression plasmids for PGISwt, PGISC441A, or a mock control expression plasmid and β-galactosidase expression plasmid. After 17 hours, the medium was changed with serum-free medium containing H-7 at various concentrations (0, 1, 10, or 100 μM). All results were obtained from three sets of experiments (n=3) and are presented as mean±S.D.

The next subject is what cascade contributes to apoptosis that is induced by prostacyclin in this system. The effect of prostacyclin on cells was tested using Iloprost (a stable prostacyclin analog) to determine the pathway inducing apoptosis. As seen in FIG. 7, when cells expressing both β-galactosidase and PGISwt or PGISC441A were treated with Iloprost at various concentrations, apoptosis was not induced even if intracellular cAMP was accumulated (FIG. 8). Both prostacyclin and Iloprost raise the intracellular level of cAMP via membrane-bound G protein-coupled prostacyclin receptor IP and/or prostaglandin E receptor EP. While, in this study, the expression of IP mRNA was not detected by RT-PCR (data not shown), it has been reported that EP is expressed in HEK-293 cells and PGB$_1$ raises the intracellular level of cAMP (Venable, M. E. et al., J. Biol. Chem. 269, 26040-26044 (1994)). Since a high concentration of prostacyclin can stimulate EP, it can be presumed that the EP-mediated stimulation by prostacyclin resulted in the accumulation of cAMP. However, it did not increase the number of apoptotic cells. Indeed, apoptosis was not enhanced in cells treated with dibutyryl-cAMP (dbcAMP) (FIG. 9). Interestingly, Iloprost and dbcAMP indeed inhibited the apoptosis in these cells to some extent (5 to 30%) (FIGS. 7 and 9). In general, apoptosis is associated with phosphorylation of cellular proteins and activation of protein kinase. Cells treated with a protein kinase inhibitor to study the relationship between protein kinase pathway and prostacyclin-mediated apoptosis. As shown in FIG. 10, H-7 (a serine-threonine protein kinase inhibitor which acts equivalently to any of cAMP-dependent protein kinase, cGMP-dependent protein kinase, and lipid-dependent protein kinase C) did not block but enhanced prostacyclin-mediated apoptosis. These data suggest that serine-threonine phosphorylation catalyzed by the kinases are not involved in the induction of prostacyclin-induced apoptosis and that the induction of prostacyclin-mediated apoptosis is not enhanced by the stimulation of G protein-coupled receptor/second messenger/protein kinase signaling pathway. The data obtained by the present inventors suggest the presence of novel prostacyclin signaling pathway which induces apoptosis independently of IP and BP.

Figure 11:
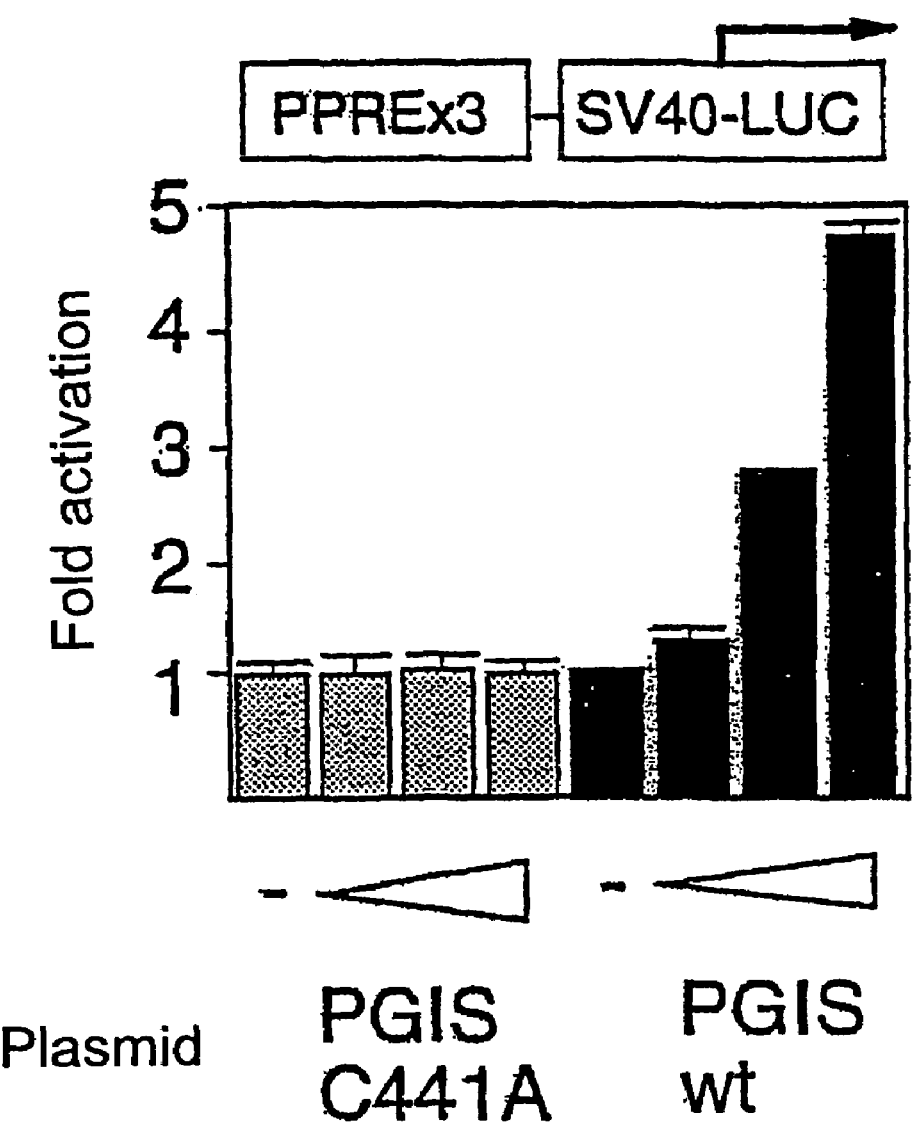
FIG. 11 is a diagram showing the influence of the expression of PGIS on PPAR activation. The degree of PPRE activation (%) was determined using PPREx3 luciferase reporter plasmid co-transfected with an expression plasmid for PGISwt or PGIS441A in various amounts (0, 0.1, 0.5, or 1 μg). The results were obtained from three sets of experiments (n=3) and are presented as mean±S.D.
Figure 12:
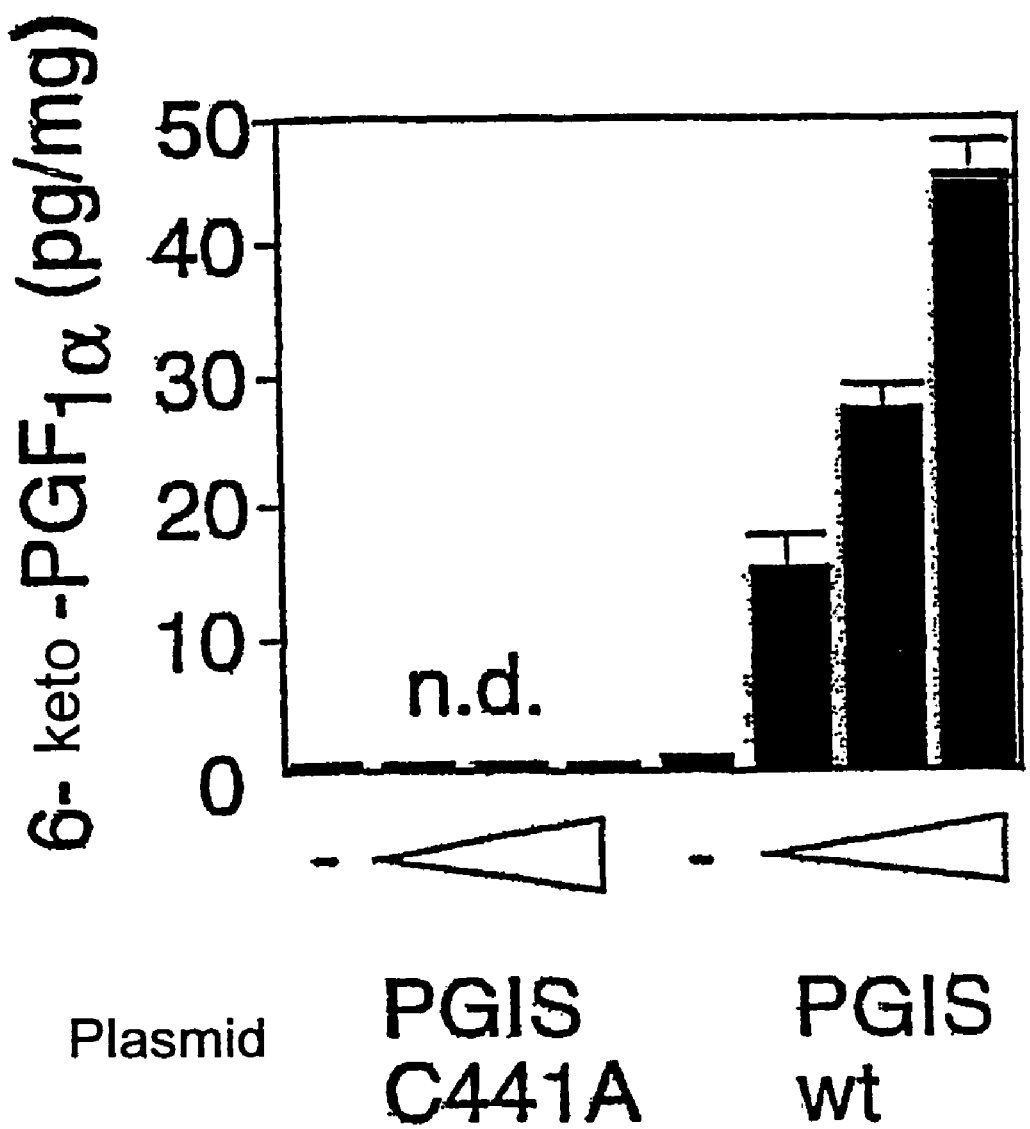
FIG. 12 is a diagram showing the influence of the expression of PGIS on the intracellular level of 6-keto-PGF$_1$α. The intracellular level of 6-keto-PGF$_1$α was determined by EIA after the cells were co-transfected with an expression plasmid for PGISwt or PGIS441A in various amounts (0, 0.1, 0.5, or 1 μg). The results were obtained from three sets of experiments (n=3) and are presented as mean±S.D.
Figure 13:
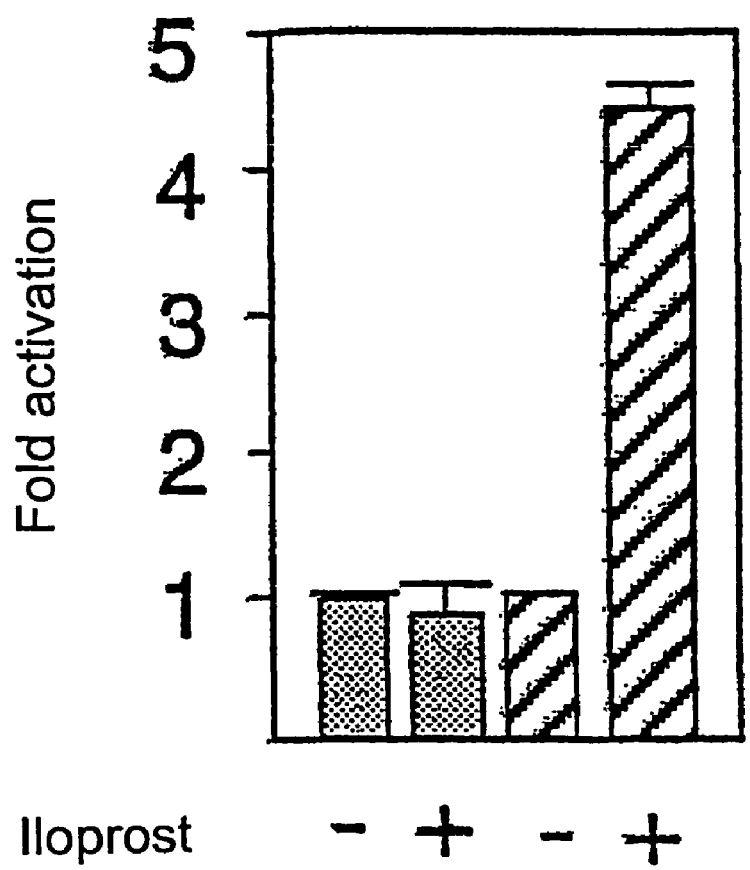
FIG. 13 is a diagram showing the influence of the expression of PGIS on PPAR activation. The effect of Iloprost (100 μM) on the degree of PPRE activation (%) was determined by using PPREx3-luciferase plasmid co-transfected with 1 μg of PGISC441A expression vector into HEK-293 cells or CV-1 cells. The results were obtained from three sets of experiments (n=3) and are presented as mean±S.D.
Figure 14:
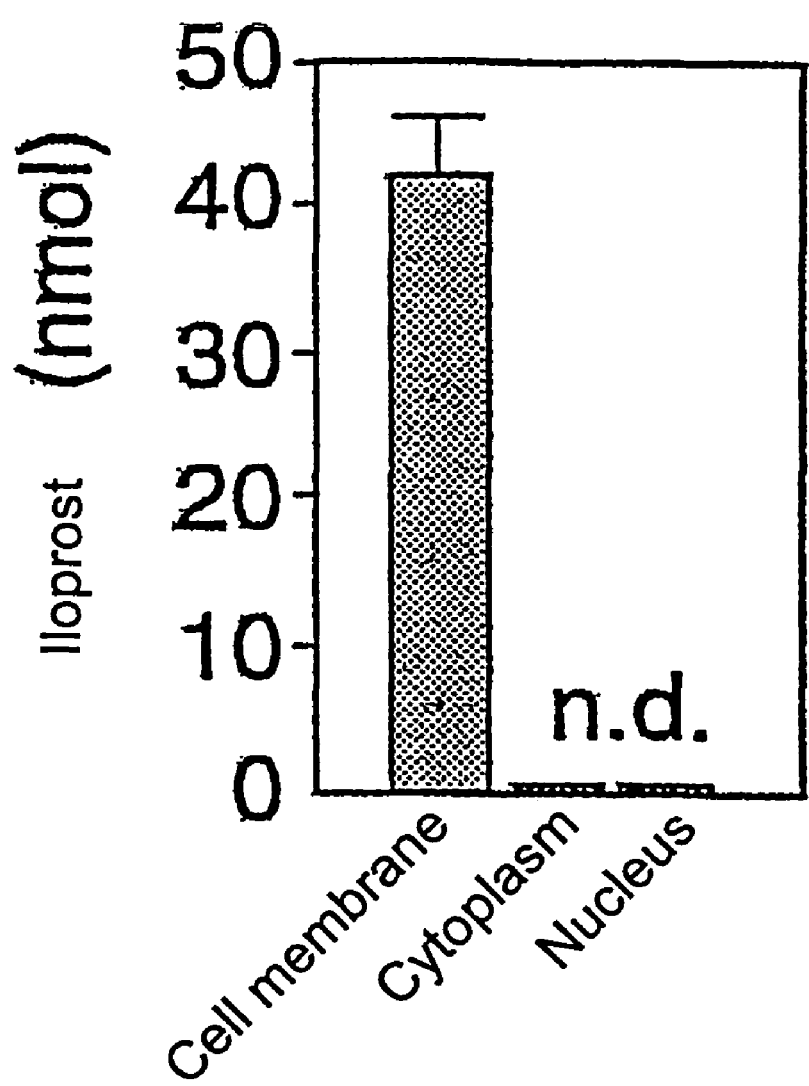
FIG. 14 is a diagram showing the influence of the expression of PGIS on PPAR activation. The permeability of Iloprost was evaluated by using $^3$H-Iloprost. HEK-293 cells were cultured in DMEM containing 100 μM $^3$H-Iloprost for 24 hours. Cell membrane, cytosol, and nuclear fractions were prepared from the cells, and then the distribution of $^3$H-Iloprost was determined using the fractions. The results were obtained from three sets of experiments (n=3) and are presented as mean±S.D.

PPAR is a member of the nuclear hormone-receptor family and itself is a ligand-activated transcription factor (Nagy, L. et al., Cell 93, 229-240 (1998)). These receptors can be activated by lipid-reducing fibrates (for example, clofibrate), various types of fatty acids, and some metabolites of arachidonic acid. The identified receptor includes three subtypes, namely PPAR-α, -δ (also known as PPAR-β or NUCI), and -γ (Braissant, O. et al. Endocrinology 137, 354-366 (1996)). PPAR is known to activate their target genes through the binding of a PPAR-RXR heterodimer to a DNA motif called PPAR-responsive element (PPRE) in the promoters of the target genes. The biology of the PPAR-δ subgroup is most poorly understood among the PPARs; Iloprost and Carbacyclin have been reported to be ligands for recombinant PPAR-δ overexpressed in CV-1 (Forman. B. M. et al., Proc. Natl. Acad. Sci. USA 94, 4312-4317 (1997)). On the other hand, it had been unclear whether an unstable eicosanoid, prostacyclin, was a native ligand for endogenous PPAR-δ because of its instability. A reporter plasmid, in which the expression of luciferase is under control of PPAR-responsive element (PPRE), was constructed to determine whether native prostacyclin can activate PPAR. In the presence of an intracellular ligand, PPAR binds to PPRE and activates the transcription of the luciferase gene, which increases luciferase activity. Cells were co-transfected with a β-galactosidase expression vector as an internal control, a PPRE-luciferase reporter plasmid, and an expression plasmid for PGISwt or PGIS441A. When the PGISwt expression plasmid and PPRE-luciferase reporter were co-transfected into cells, luciferase activity was increased in parallel with the level of intracellular 6-keto-of $PGF_1\alpha$ (FIGS. 11 and 12). Co-transfection of the PGISC441A and reporter into cells did not result in neither production of 6-keto-of $PGF_1\alpha$ nor induction of luciferase activity. As seen in FIG. 13, Iloprost (1 to 100 µM) could not increase the activity of PPRE-luciferase in this system. Many types of PG have been believed to be transported via PC transporter across the cell membrane into cells (Kanai, N. et al., Science 268, 866-869 (1995)). On the other hand, it has been reported that Iloprost is hardly transported into cells by the PG transporter (Chan, B. S. et al., J. Biol. Chem. 273, 6689-6697 (1998)). The present inventors also confirmed that Iloprost taken up by HEK-293 cells is very little and most of the Iloprost incorporated (99%<) is localized on cell membrane (FIG. 14). Prostacyclin added to medium could not activate recombinant PPAR overexpressed in CV-1 cells; it has been reported that addition of Iloprost results in activation of recombinant PPAR overexpressed in cells (Hertz, R. et al., Bur. J. Biochem. 235, 242-247 (1996)). The data obtained by the present inventors indicated that Iloprost added to culture medium could not activate endogenous PPAR expressed in HEK-293 cells. HEK-293 cell can serve as an excellent model to characterize intracellular and extracellular signaling discriminately. From these observations, it can be concluded that intracellular prostacyclin produced by PGISwt activates PPAR and thus induces apoptosis but extracellular prostacyclin does not induce apoptosis.

Iloprost serves as a ligand for both PPAR-α and -δ. PPAR-α is expressed in hepatocyte, myocardial cell, intestinal cells, and cells of kidney proximal tubule at high levels (Tone, Y. et al., Bur. J. Cell. Biol. 72, 268-277 (1997)). PPAR-α can inhibit apoptosis in hepatocyte (Carcinogenesis, 19, 43-48 (1998)) and enhance apoptosis in human macrophages activated by TNF-α (Chinetti, G. et al., J. Biol. Chem. 273. 25573-25580 (1998)). On the other hand, PPAR-δ is expressed ubiquitously and often at higher levels than PPAR-α and PPAR-γ (Endocrinology 139, 2748-2754 (1998)). Further, biological and physiological functions of PPAR-δ remain to be clarified. Antisense oligonucleotides for these PPARs were used to identify the apoptosis-enhancing signaling pathway activated by prostacyclin. When the antisense oligonucleotide PPAR-α was transfected into HEK-293 cells using HVJ-liposome method (Todaka, T. et al., Stroke 30, 419-426 (1999)), apoptosis was not inhibited and actually the cell viability declined (data not shown). In contrast, transfection of the cells with a PPAR-α sense oligonucleotide, which was carried out by the same method, resulted in no marked changes in the cells. These results demonstrate that PPAR-α can play an important role to maintain survival of HEK-293 cells and prostacyclin-mediated apoptosis is not enhanced via PPAR-α.

Figure 15:
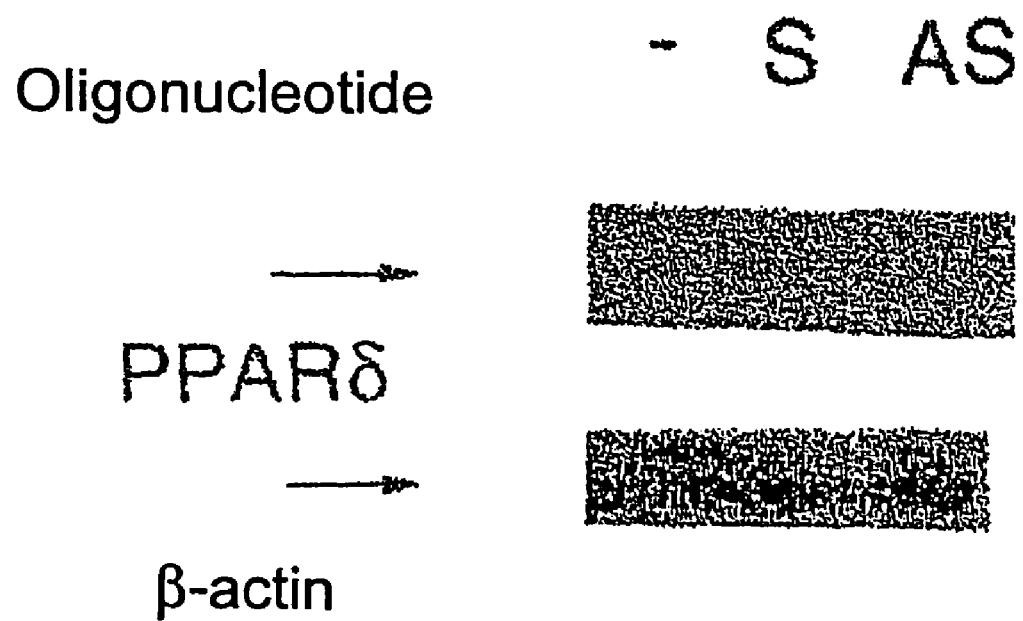
FIG. 15 shows a photographic pattern indicating suppression of PPAR-δ expression by an antisense oligonucleotide. A lysate prepared from cells transfected with the PPAR-δ antisense oligonucleotide (AS) was immuno-blotted using an anti-PPAR-δ monoclonal antibody; a sense oligonucleotide (S) was used as a control.
Figure 16:
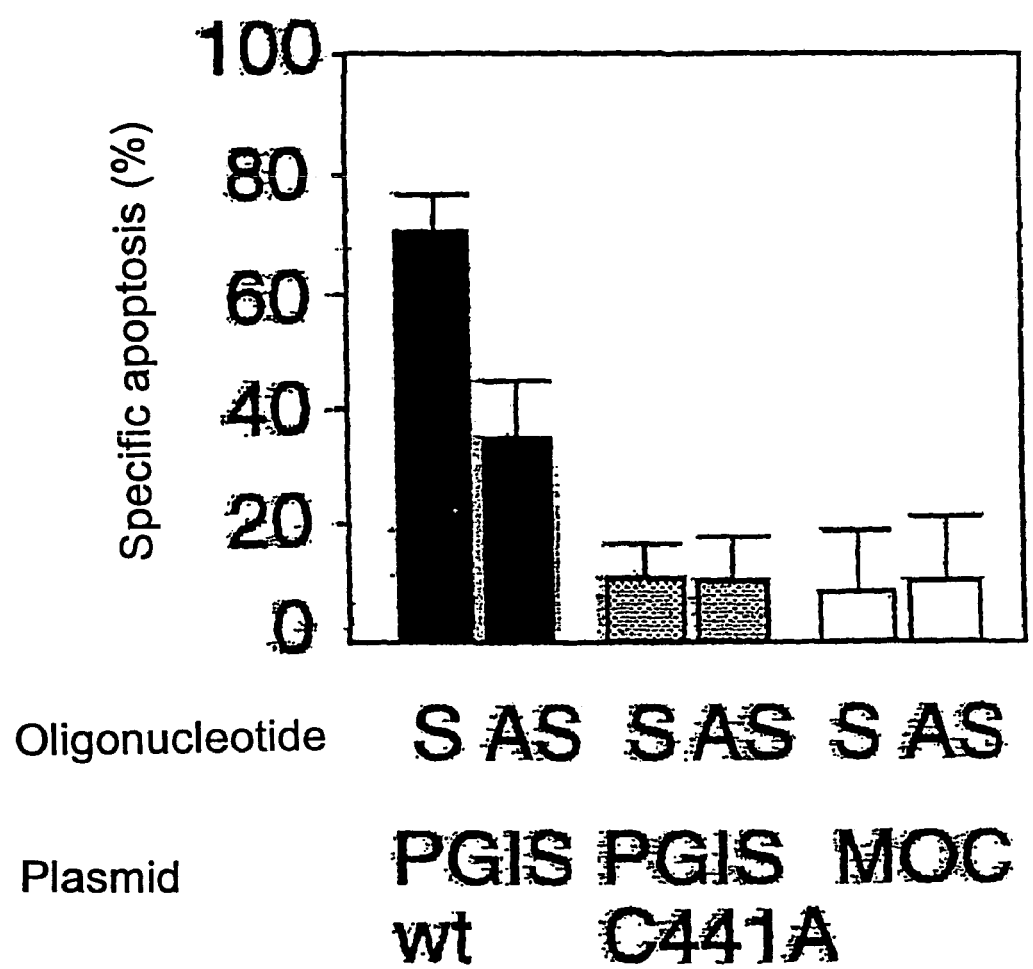
FIG. 16 illustrates a diagram showing an influence of PPAR-δ suppression by using the PPAR-δ antisense oligonucleotide (AS) on prostacyclin-mediated apoptosis induced through the expression of PGIS. A sense oligonucleotide (S) was used as a control.
Figure 17:
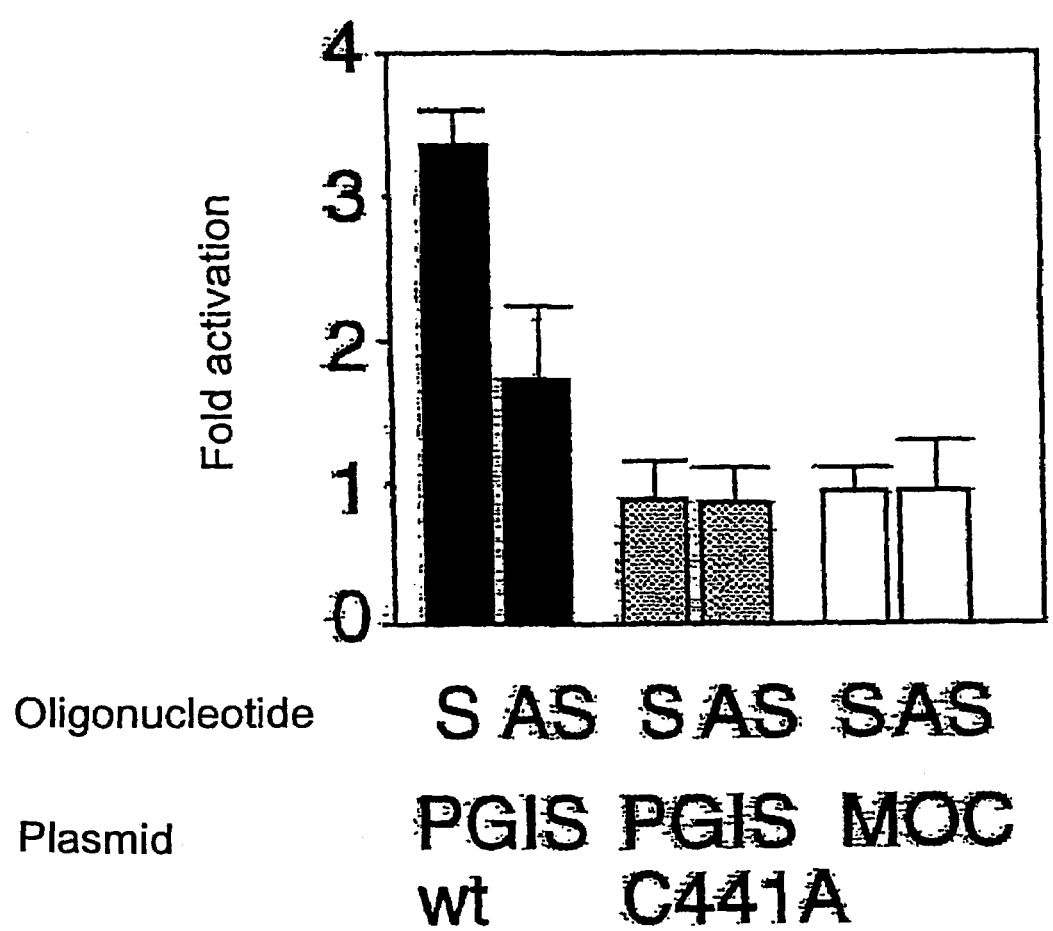
FIG. 17 is a diagram showing an influence of PPAR-δ suppression by using the PPAR-δ antisense oligonucleotide (AS) on PPAR activation induced through the expression of PGIS.
Figure 18:
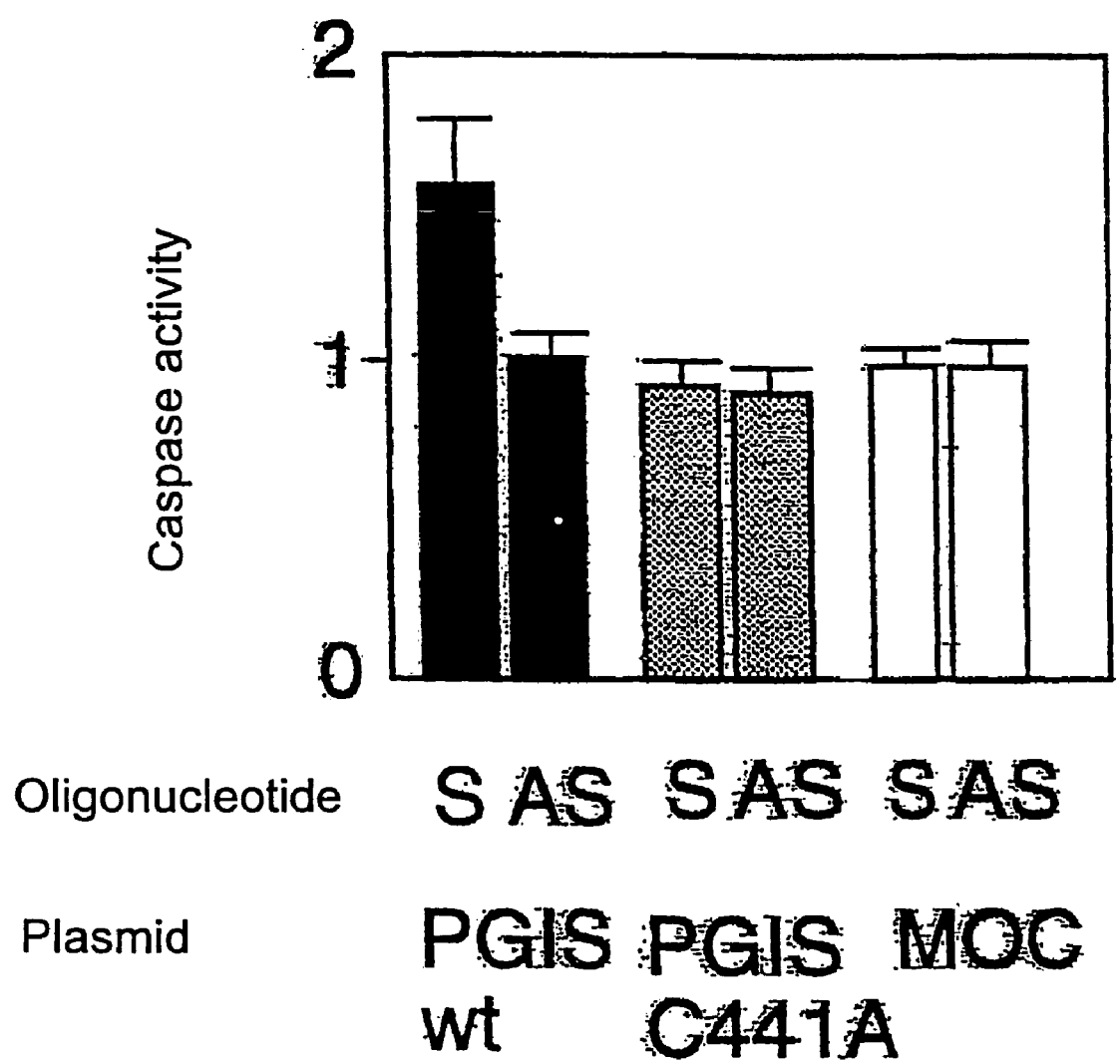
FIG. 18 is a diagram showing an influence of PPAR-δ suppression by using the PPAR-δ antisense oligonucleotide (AS) on caspase activity. All results were obtained from three sets of experiments (n=3) and are presented as mean±S.D.

Thus, the present inventors predicted that PPAR-δ was the second prostacyclin receptor that was a important molecule involved in prostacyclin-mediated apoptosis. To directly test this hypothesis, the present inventors carried our transfection of HEK-293 cells with a PPAR-δ antisense oligonucleotide using HVJ-liposome method. Using immunoblotting, the production of PPAR-δ protein was confirmed to be suppressed after 48 hours (FIG. 15). The cells treated with the PPAR-δ antisense oligonucleotide showed normal morphology; the number of cells was increased. When the PGISwt expression vector and β-galactosidase expression vector were co-transfected with the antisense oligonucleotide into cells, prostacyclin-mediated apoptosis was significantly blocked; the blockage was evaluated based on the decreased number of apoptotic cells containing the antisense oligonucleotide (FIG. 16). Further, the activity of luciferase, which had been co-expressed with PGISwt, was significantly decreased in cells treated with the PPAR-δ antisense oligonucleotide. These results clearly demonstrate that not only Iloprost and Carbaprostacyclin but also prostacyclin is also a ligand for PPAR-δ. As seen in FIGS. 17 and 18, luciferase activity increased in parallel with the increase in caspase activity. These results also demonstrate that prostacyclin-mediated apoptosis depends on the expression of endogenous PPAR-δ.

Figure 19:
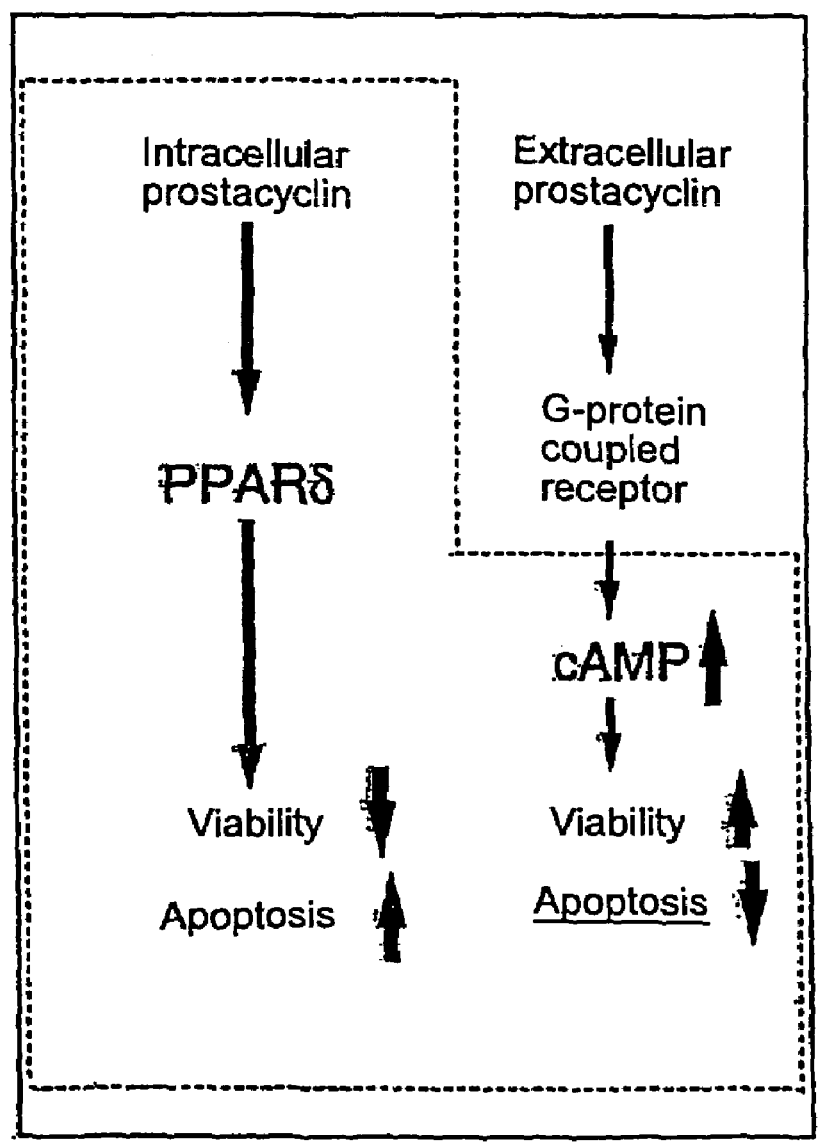
FIG. 19 shows a model of prostacyclin signaling pathway including the nuclear receptor PPAR-δ, which exerts a reverse effect to the one given via cAMP signaling pathway in the control of cells fate.

The present inventors demonstrated for the first time that prostacyclin was authentic, natural ligand for PPAR-δ and activation of endogenous PPAR-δ by prostacyclin resulted in activation of apoptotic pathway in HEK-293 cells. Prostacyclin interacts with both nuclear PPAR-δ and cell-surface receptor and raises the intracellular level of cAMP; these two types of signaling respectively produce reverse biological effects on apoptosis and/or cell survival in a synergistic fashion. As shown in the multi-diagrams in FIG. 19, the present inventors focused on the prostacyclin signaling pathway including nuclear receptor PPAR-δ. Why the endogenous agent does not induce apoptosis in PGIS-expressing endothelial cells and vascular smooth muscle cells? The reason is that endothelial cells and vascular smooth muscle cells express also endogenous prostacyclin receptor (IP) (which raises the level of cAMP in the presence of prostacyclin at a low concentrations). IP/cAMP/protein kinase pathway is presumed to protect these cells from prostacyclin-mediated apoptosis by an autocrine and/or paracrine mechanism. Thus, it can be assumed that prostacyclin-mediated apoptosis is readily induced in cells lacking IP expression, such as HEK-293 and CV-1. Further, there may be a precise mechanism in which cell fate is regulated by prostacyclin in cooperation with PPAR-α, PPAR-δ, and G protein-coupled PG receptor. The research group of the present inventors is now characterizing the prostacyclin-signaling cascade including the novel pathway.

[EXAMPLE 2] INDUCTION OF APOPTOSIS IN HUMAN COLON CANCER CELLS

The wild-type PGIS gene (PGISwt) or inactive PGIS gene (PGISC441A) prepared by introducing alanine into the active center of PGIS by conventional site-directed mutagenesis were transfected into cells of the human colon cancer cell line Caco2. 1.0 µg of β-galactosidase expression vector was co-transfected with the above-mentioned gene into the cells using LipofectAMINE. Control transfection experiments were carried out using HEK-293 cells and CV-1 cells by the same procedure. After 60 hours, the cells were stained with X-gal. The results are shown in FIG. 20.

Figure 20:
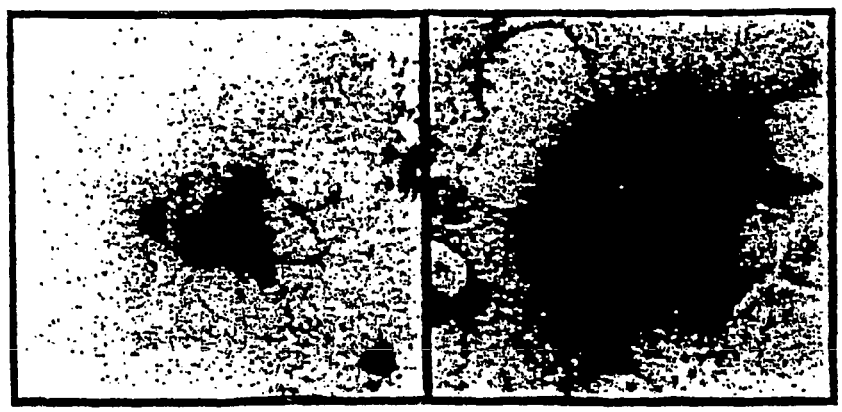
FIG. 20 shows photographic patterns of results obtained by transfecting an inactive PGIS gene (PGISC441A) or the native PGIS gene (PGISwt) into cells of human colon cancer cell line Caco2.
Figure 20:
Figure 20:

As seen in FIG. 20, apoptosis was recognized only in cells in which PGISwt had been introduced. Thus, it is demonstrated that the introduced PGIS gene induces apoptosis in cancer cells and the PGIS gene can be effective in treating cancers.

[EXAMPLE 3] ASSESSMENT OF CANCER THERAPY USING INTRODUCTION OF THE PGIS Gene

The PGIS gene was inserted into adenoviral vector by the conventional method to prepare a recombinant adenoviral vector. The recombinant vector obtained is used as a pharmaceutical composition for gene therapy of a cancer.

(1) Animal Experiments

The pharmaceutical composition for gene therapy is administered in adequate dose at appropriate administration frequency (1, 2, or 3 times) to a nude mouse as a cancer model in which tumor formation has been confirmed; an alteration in tumor diameters is observed at the same time. A control group is administered adenoviral vector without the prostacyclin synthase gene. Further, to assess the dose or frequency of administration, one can use several different groups where the dose or frequency of administration is varied appropriately. When tumor formation is confirmed, then tumor size is measured in both group administered the pharmaceutical composition of the present invention for inducing apoptosis (treated group) and control group.

When tumor involution is seen in the treated group, the involution serves as an index of therapeutic achievement of cancer therapy at the level of animal experiment. In addition, tissues can be assessed by the about-described method for assessing characteristics of apoptosis. When many apoptotic cells are seen in the treated group, the presence of apoptotic cells serves as an index of apoptosis-inducing activity of the pharmaceutical composition of the present invention for inducing apoptosis at the level of animal experiment.

(2) Clinical Test in Human Individuals

The pharmaceutical composition for gene therapy is administered in adequate dose at appropriate administration frequency. Then, the recombinant adenoviral vector should be tested for the cytotoxicity, infectivity to other individuals, and integration into the chromosome of viral vector according to the descriptions in "Handbook for Development and Research of Gene Therapy (Ed. The Japanese society of Gene Therapy; NTS, 1999)".

The clinical effects of cancer therapy on individuals are evaluated based on an assessment index of tumor by periodically recording photographic images, CT scan images, MRI images or the like of tumors; by measuring diameters of tumor; and by estimating tumor volume based on the orthogonal major and minor axes to determine tumor growth rates. Additionally, the presence of apoptosis is assessed by morphological observations on the tissues. Further, analysis techniques of molecule biology can be utilized; the presence of a DNA as the active ingredient in target cells can be confirmed by the detection method using PCR; apoptosis can be detected by TUNEL staining.

[EXAMPLE 4] SCREENING FOR AGENTS THAT INDUCE APOPTOSIS IN CELLS

The oligonucleotide, describe in Example 1, containing three copies of PPRE, which is a PPAR-responsive element, is ligated to a reporter gene to prepare a plasmid. The luciferase gene is used as the reporter gene; pGL3-promotor vector (Promega) is used as the plasmid.

Then, the above-mentioned plasmid is introduced into cells to prepare transformed cells. In this experiment, HEK-293 cell (ATCC CRL-1573), which expresses endogenous PPAR-δ and allows detection of reporter gene activity, is used as the host. The delivery of the plasmid into cells is carried out by the method using LipofectAMINE (Gibco-BRL).

A candidate for the agent that induces apoptosis can be selected by adding a test substance to transformed cells thus prepared, and measuring and assessing whether the test substance increases the expression level of the reporter gene. A test substance that increases the expression level of the reporter gene is a candidate for the agent that induces apoptosis. Thus, an agent that induces apoptosis in cells can be selected by further subjecting such selected candidate test substances to apoptosis assay or the like using, as an index, caspase activity as describe in Example 1.

Sequence Listing Free Text

SEQ ID NO: 1 is an amino acid sequence for synthetic peptide corresponding to amino acid NOs: 27 to 45 of human PGIS.

SEQ ID NO: 2 is an amino acid sequence for synthetic peptide corresponding to amino acid NOs: 485 to 500 of human PGIS.

SEQ ID NO: 3 is a nucleotide sequence of oligonucleotide for HVJ-lyposome method.

SEQ ID NO: 4 is a nucleotide sequence of oligonucleotide for HVJ-lyposome method.

SEQ ID NO: 5 is a nucleotide sequence of oligonucleotide for HJV-lyposome method.

SEQ ID NO: 6 is a nucleotide sequence of oligonucleotide for HVJ-lyposome method.

SEQ ID NO: 7 is a nucleotide sequence of oligonucleotide for PPREx3-luciferase assay.

SEQ ID NO: 8 is a nucleotide sequence of oligonucleotide for PPREx3-luciferase assay.

INDUSTRIAL APPLICABILITY

The pharmaceutical composition of the present invention for inducing apoptosis produces an excellent therapeutic effect in which the diseases can be treated by inducing apoptosis. In addition, the pharmaceutical composition of the present invention for gene therapy of cancer can induce apoptosis and thereby cell death of cancer cells can be induced. Further, the screening method of the present invention can be used conveniently to screen for agents capable of inducing apoptosis.

What is claimed is:

1. A method for inducing apoptosis in a cancer cell, said method comprising administering to the cancer cell a pharmaceutical composition that comprises a nucleic acid encoding and expressing a prostacyclin synthase as an active ingredient, wherein said pharmaceutical composition is used in combination with an additional agent comprising a nucleic acid encoding and expressing a cyclooxygenase-2.

2. The method according to claim 1, wherein the cancer is solid cancer.

3. The method of claim 2, wherein the cancer is kidney cancer.

4. The method of claim 2, wherein the cancer is colon cancer.

* * * * *

SEQUENCE LISTING

<160> NUMBER OF SEQ ID NOS: 8

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence:synthetic
      peptide P1 corresponding to amino acids 27-45 of
      human prostacyclin synthase (PGIS)

<400> SEQUENCE: 1

Pro Gly Glu Pro Pro Leu Asp Leu Gly Ser Ile Pro Trp Leu Gly Tyr
 1               5                  10                  15

Ala Leu Asp Cys
            20

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence:synthetic
      peptide P4 corresponding to amino acids 485-500 of
      human prostacyclin synthase (PGIS)

<400> SEQUENCE: 2

Leu Met Gln Pro Glu His Asp Val Pro Val Arg Tyr Arg Ile Arg Pro
 1               5                  10                  15

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:human
      peroxisome proliferator-activated receptor delta
      (PPAR-delta) cDNA sense sequence oligonucleotide
      dS for HJV-liposome method

<400> SEQUENCE: 3
ctcggtgact tatcctgtg                                              19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:human
      peroxisome proliferator-activated receptor delta
      (PPAR-delta) cDNA antisense sequence
      oligonucleotide dAS for HJV-liposome method

<400> SEQUENCE: 4
tcctctttct cctcctctt                                              19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:human
      peroxisome proliferator-activated receptor alpha
      (PPAR-alpha) cDNA sense sequence oligonucleotide
      aS for HJV-liposome method

```
<400> SEQUENCE: 5
ctcggtgact tatcctgtg                                              19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:human
      peroxisome proliferator-activated receptor alpha
      (PPAR-alpha) cDNA antisense sequence
      oligonucleotide aAS for HJV-liposome method

<400> SEQUENCE: 6
cacaggataa gtcaccgag                                              19

<210> SEQ ID NO 7
<211> LENGTH: 67
<212> TYPE: DNA
<213> ORGANISM: Artificial Sequence
<220> FEATURE:
<223> OTHER INFORMATION: Description of Artificial Sequence:sense
      oligonucleotide for PPAR-responsive element (PPRE)
      PPREx3-luciferase assay

<400> SEQUENCE: 7
cgcgtaaaaa ctgggccaaa ggtctcaaaa actgggccaa aggtctaaaa actgggccaa    60
aggtctc                                                           67

<210> SEQ ID NO 8
<211> LENGTH: 65
<212> TYPE: DNA
<213> ORGANISM: Artificial Sequence
<220> FEATURE:
<223> OTHER INFORMATION: Description of Artificial Sequence:antisense
      oligonucleotide for PPAR-responsive element (PPRE)
      PPREx3-luciferase assay

<400> SEQUENCE: 8
tcgagagacc tttggcccag tttttagacc tttggcccag tttttagacc tttggcccag    60
tttta                                                             65
```